US011980496B2

(12) United States Patent
Zhao et al.

(10) Patent No.: US 11,980,496 B2
(45) Date of Patent: May 14, 2024

(54) PUNCTURE NEEDLE POSITIONING SYSTEM AND METHOD

(71) Applicant: Tianli Zhao, Hu'nan (CN)

(72) Inventors: Tianli Zhao, Hu'nan (CN); Heng Luo, Hu'nan (CN); Shijun Hu, Hu'nan (CN); Jintao Xiao, Hu'nan (CN); Jianyuan Ke, Hu'nan (CN)

(73) Assignee: Tian Li, Hu'nan (CN)

( * ) Notice: Subject to any disclaimer, the term of this patent is extended or adjusted under 35 U.S.C. 154(b) by 170 days.

(21) Appl. No.: 17/334,951

(22) Filed: May 31, 2021

(65) Prior Publication Data
US 2021/0282743 A1 Sep. 16, 2021

Related U.S. Application Data

(63) Continuation of application No. PCT/CN2020/091532, filed on May 21, 2020.

(30) Foreign Application Priority Data

Feb. 4, 2020 (CN) .......................... 202010079870.8
Feb. 4, 2020 (CN) .......................... 202010079873.1
Feb. 4, 2020 (CN) .......................... 202020151840.9

(51) Int. Cl.
A61B 8/12 (2006.01)
A61B 8/00 (2006.01)
(Continued)

(52) U.S. Cl.
CPC ................ *A61B 8/12* (2013.01); *A61B 8/085* (2013.01); *A61B 8/4254* (2013.01);
(Continued)

(58) Field of Classification Search
CPC ................ A61B 17/34; A61B 17/3403; A61B 2017/3413; A61B 2034/107;
(Continued)

(56) References Cited

U.S. PATENT DOCUMENTS 6,216,029 B1 * 4/2001 Paltieli .................... A61B 34/20
600/461
2002/0156363 A1 * 10/2002 Hunter .................. G06T 3/0068
600/410
(Continued)

FOREIGN PATENT DOCUMENTS

WO WO-2021065956 A1 * 4/2021

OTHER PUBLICATIONS

Translated FOR Sakamoto (WO 2021065956 A1) (Year: 2021).*

Primary Examiner — Katherine L Fernandez
Assistant Examiner — Brooke Lyn Klein
(74) Attorney, Agent, or Firm — Global IP Services; Tianhua Gu

(57) ABSTRACT

The invention relates to the technical field of surgical positioning, in particular to a puncture needle positioning system and method, and a method and device for obtaining the axis of an ultrasound probe as projected onto an ultrasound image. The puncture needle positioning system includes: an ultrasound unit including a first probe for providing an ultrasound image of a lesion, and a plurality of first positioning devices for providing coordinate information of the first probe are provided on the first probe; the needle unit includes a puncture needle. The puncture needle is provided with a plurality of second positioning devices for providing coordinate information of the puncture needle; a processing and display unit is connected to the ultrasound (Continued)

unit, each of the first positioning devices, and each of the second positioning devices. The puncture needle positioning system improves the accuracy of transthoracic puncture, thereby avoiding complications caused by repeated puncture.

9 Claims, 8 Drawing Sheets

(51) Int. Cl.
    *A61B 8/08*     (2006.01)
    *A61B 17/34*     (2006.01)
    *A61B 34/10*     (2016.01)
    *A61B 90/00*     (2016.01)

(52) U.S. Cl.
    CPC ............ *A61B 8/4444* (2013.01); *A61B 8/461* (2013.01); *A61B 2017/3413* (2013.01); *A61B 2034/107* (2016.02); *A61B 2090/378* (2016.02)

(58) Field of Classification Search
    CPC ...... A61B 2034/2051; A61B 2090/378; A61B 2090/3784; A61B 34/20; A61B 8/0841; A61B 8/085; A61B 8/0883; A61B 8/12; A61B 8/4254; A61B 8/4444; A61B 8/461; A61B 8/5207; A61B 8/5223

See application file for complete search history.

(56) References Cited

U.S. PATENT DOCUMENTS

| | | | | |
|---|---|---|---|---|
| 2003/0000535 A1* | 1/2003 | Galloway, Jr. | .......... | A61B 34/20 606/41 |
| 2005/0090742 A1* | 4/2005 | Mine | ................. | A61B 17/3403 600/443 |
| 2005/0090746 A1* | 4/2005 | Ohtake | ............... | A61B 8/4254 600/447 |
| 2007/0055142 A1* | 3/2007 | Webler | ................... | A61B 5/062 600/425 |
| 2010/0204579 A1* | 8/2010 | Yoshida | .............. | G01S 7/52074 600/443 |
| 2016/0100821 A1* | 4/2016 | Eggers | .................... | A61B 8/54 600/424 |
| 2016/0199023 A1* | 7/2016 | Pelissier | ............... | G06T 7/0016 600/424 |
| 2017/0372640 A1* | 12/2017 | Lampotang | ............. | G09B 9/00 |
| 2019/0110848 A1* | 4/2019 | Popovic | ........................ | A61F 2/2427 |
| 2021/0133942 A1* | 5/2021 | Wang | ........................ | G06T 7/30 |
| 2021/0307723 A1* | 10/2021 | Paltieli | ..................... | A61B 8/12 |

* cited by examiner

PUNCTURE NEEDLE POSITIONING SYSTEM AND METHOD

CROSS REFERENCE TO RELATED APPLICATIONS

The present application is a bypass US national phase of PCT/CN2020/091532, claims the benefit of priorities to Chinese Patent Application No. CN 2020100798731, entitled "PUNCTURE NEEDLE POSITIONING SYSTEM AND METHOD", filed with CNIPA on Feb. 4, 2020, Chinese Patent Application No. CN 2020100798708, entitled "METHOD AND DEVICE FOR POSITIONING THE AXIS OF AN ULTRASOUND PROBE AS PROJECTED ONTO A PLANE CONTAINING AN ULTRASOUND IMAGE", filed with CNIPA on Feb. 4, 2020, and Chinese Patent Application No. CN 2020201518409, entitled "POSITIONING DEVICE", filed with CNIPA on Feb. 4, 2020, the disclosures of which are incorporated herein by reference in their entireties.

FIELD OF TECHNOLOGY

The present disclosure generally relates to surgical positioning, in particular to a puncture needle positioning system and method.

BACKGROUND

Transthoracic puncture intracardiac interventional therapy is an emerging interventional technology. Its interventional paths are short, straight, and close to lesions. It makes it easy for medical staff to precisely manipulate interventional instruments. It is suitable for a variety of operations for structural heart disease, especially for post-surgery complications. The key of this technology is to select precise puncture sites and paths to ensure success at first try. If the heart is punctured repeatedly, serious complications such as pericardial tamponade due to bleeding from the puncture point(s) will result. For this reason, preoperative transthoracic ultrasound scanning is needed to plan a puncture path and determine puncture sites and spatial position of the puncture needle. Generally speaking, after the ultrasound scanning has determined the lesion's location, the best puncture path is along the axis of the fan-shaped ultrasound image that goes through the lesion. However, in reality, the medical staff can only reconstruct the spatial position of the puncture needle in their mind based on their personal experience. Therefore, there is a high risk of incorrectly selecting the positions of the puncture point and the puncture needle, which leads to serious complications. In order to improve the success rate of puncturing, it is necessary to record and visualize the planned puncture path for intraoperative reference.

SUMMARY

The invention relates to the technical field of surgical positioning, in particular to a puncture needle positioning system and method, and a method and device for obtaining the axis of an ultrasound probe as projected onto an ultrasound image.

The puncture needle positioning system includes: an ultrasound unit including a first probe for providing an ultrasound image of a lesion, and a plurality of first positioning devices for providing coordinate information of the first probe are provided on the first probe; the needle unit includes a puncture needle. The puncture needle is provided with a plurality of second positioning devices for providing coordinate information of the puncture needle; a processing and display unit is connected to the ultrasound unit, each of the first positioning devices, and each of the second positioning devices.

The puncture needle positioning system improves the accuracy of transthoracic puncture, thereby avoiding complications caused by repeated puncture.

DESCRIPTION OF COMPONENT MARK NUMBERS

Figure 1:
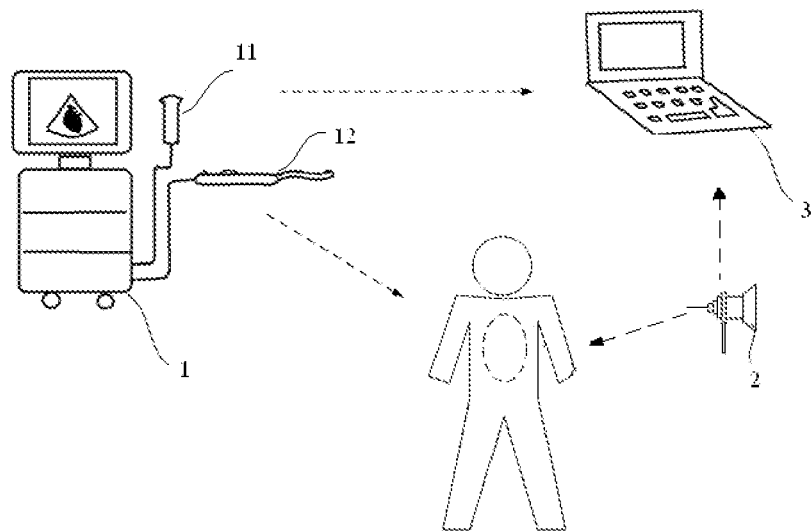
FIG. 1 shows an application scenario of a puncture needle positioning system according to some embodiments of the present disclosure.

1 Ultrasound unit
11 First probe
12 Second probe
2 Puncture needle unit
3 Processing and display unit
4 First positioning device
5 Second positioning device
6 Probe clamp
7 Puncture needle clamp
8 Ultrasound probe
9 Positioning device

DETAILED DESCRIPTION

One or more specific embodiments of the present disclosure will be described below. These described embodiments are only examples of the presently disclosed techniques, and are not intended to limit aspects of the presently disclosed invention. Additionally, in an effort to provide a concise description of these embodiments, all features of an actual implementation may not be described in the specification. It should be appreciated that in the development of any such actual implementation, numerous implementation-specific decisions must be made to achieve the developers' specific goals, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 2:
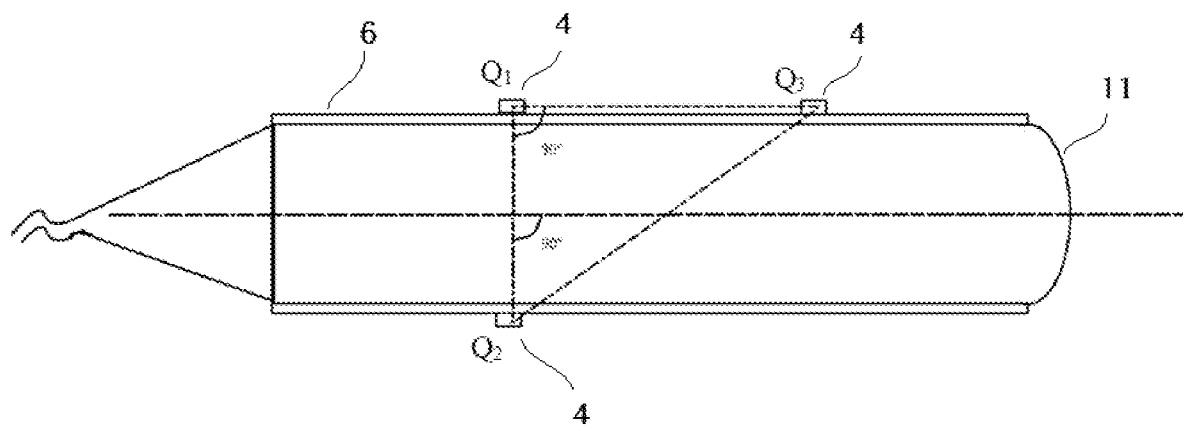
FIG. 2 is a schematic diagram of the structure of a first probe according to some embodiments of the present disclosure.
Figure 4:
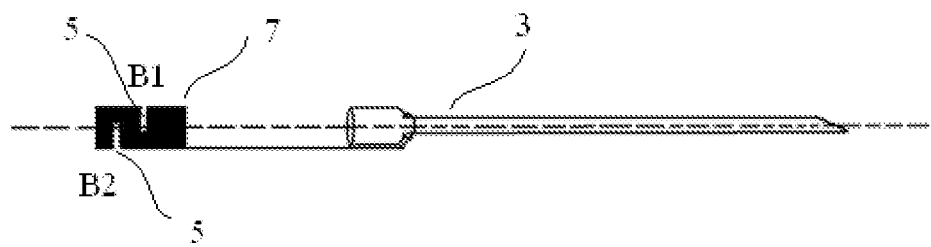
FIG. 4 is a schematic diagram of the structures of a puncture needle and a puncture needle fastener according to some embodiments of the present disclosure.
Figure 5:
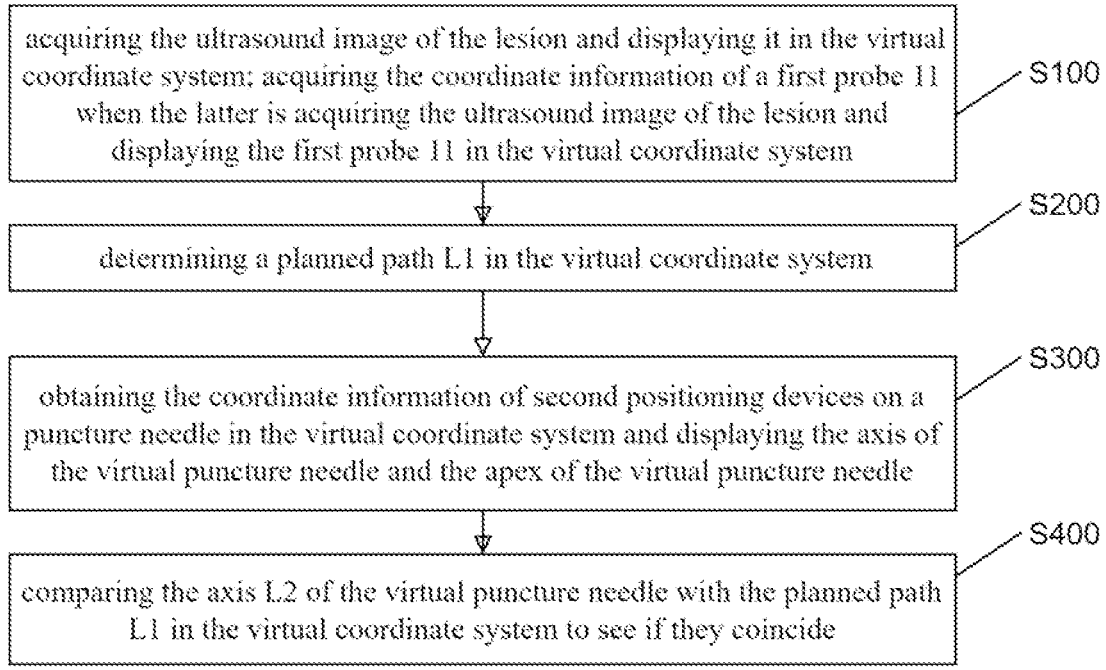
FIG. 5 is a schematic flow chart illustrating a puncture needle positioning method according to some embodiments of the present disclosure.

As shown in FIG. 1, the present disclosure provides a puncture needle positioning system. As shown in FIG. 1, the system includes: an ultrasound unit 1, a puncture needle unit 2, a processing and display unit 3. The ultrasound unit 1 includes a first probe 11 for providing an ultrasound image of a lesion. The first probe 11 obtains the ultrasound image by directing sound waves at the lesion and receiving sound waves reflected back from the lesion thereby obtaining data representing the ultrasound image of the lesion. As shown in FIG. 2, the first probe 11 is provided with a plurality of first positioning devices 4 for providing coordinate information of the first probe 11. The puncture needle unit 2 includes a puncture needle. As shown in FIG. 4, the puncture needle is provided with a plurality of second positioning devices 5 for providing coordinate information of the puncture needle. The processing and display unit 3 is in communication connection with the ultrasound unit 1, each of the first positioning devices 4, and each of the second positioning devices 5, and the processing and display unit 3 may obtain the ultrasound image of the lesion and display it in a virtual coordinate system; obtain the coordinate information of the first probe 11 when it is acquiring the ultrasound image of the lesion, and display the coordinate information in the virtual coordinate system; determine a planned path L1 in the virtual coordinate system; obtain the coordinate information of the second positioning device 5 on the puncture needle in the virtual coordinate system; display the axis L2 of a virtual puncture needle and the apex C2 of the virtual puncture needle; compare the axis L2 of the virtual puncture needle and the planned path L1 to see if they coincide. When the axis L2 of the virtual puncture needle coincides with the planned path L1, the puncture needle is ready to be used for puncturing. The virtual puncture needle is the virtual counterpart of the puncture needle in the virtual coordinate system, and is determined at least partially by the second positioning devices 5; the same with the virtual first probe. The coordinate information provided by different sets of positioning devices may have different points in space as the origin; therefore the relative positions of the virtual counterparts of the first probe, the puncture needle, etc. in the virtual coordinate system may not correspond to their relative positions in real life.

The ultrasound unit 1 may be an ultrasound machine with multiple probes. As shown in FIG. 2, the ultrasound unit 1 includes a first probe 11 for providing an ultrasound image of the lesion, and the first probe 11 is a transthoracic cardiac ultrasound probe. Herein, an "ultrasound image" refers to an image showing an anatomic portion of anatomy being visualized by an ultrasound probe. The first probe can be a conventional ultrasound probe, such as Philips EPIQ7C. When in use, the first probe 11 scans the intercostal space of the human body for any lesion such as a ventricular septal defect, to obtain an ultrasound image of the lesion.

Figure 3:
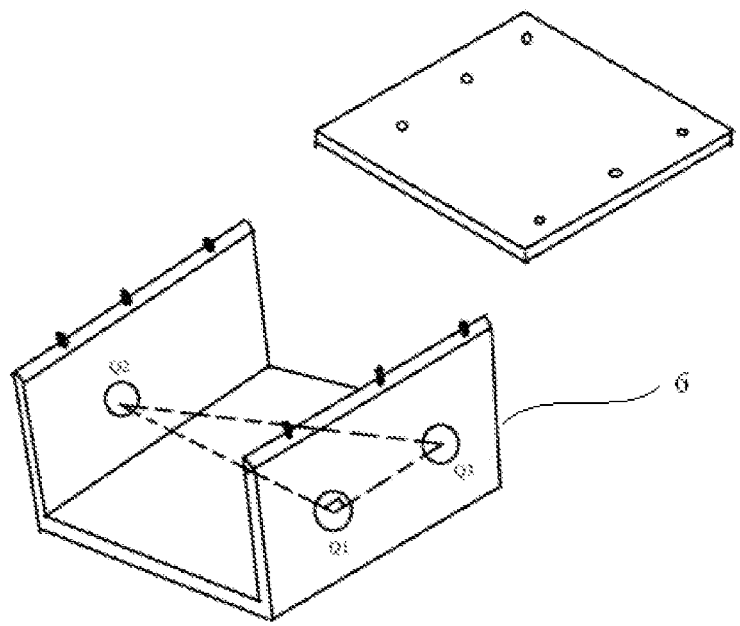
FIG. 3 is a schematic diagram of a clamp structure of an ultrasound probe according to some embodiments of the present disclosure.

The first probe 11 is provided with a plurality of first positioning devices 4 for providing coordinate information of the first probe 11. The coordinate information of the first probe 11 includes the coordinate information of several position points on the first probe 11. The position points are selected to facilitate the determination of location points of the axis of the first probe 11. In one embodiment, as shown in FIG. 2, the first probe 11 is provided with three first positioning devices 4, and the three first positioning devices 4 are located on the same plane which coincides with the axis of the first probe 11, wherein two of the first positioning devices 4 are on the cutting plane of a cross section of the first probe 11, the cross section is perpendicular to the axis, and the three first positioning devices 4 constitute the vertices of a right triangle. This arrangement is for determining the axis of the first probe 11 by the first positioning devices 4. The first positioning devices 4 are selected from sensors. Normally, the sensors are used in conjunction with a magnetic source and a magnetic locator, with the sensors in communication with the magnetic locator, and the magnetic source in communication with the magnetic locator. When in use, the magnetic source is located near an operating table. In one embodiment, 3DGuidance trakSTAR of the Canadian company Northern Digital Incorporated (NDI) is used. The 3DGuidance trakSTAR device includes the sensor, magnetic source, and magnetic locator used in the present disclosure. Further, for the installation stability of the first probe 11 and the first positioning devices 4, the first probe 11 is provided with a probe clamp 6 that is matched with the first probe 11. The probe clamp 6 is shown in FIG. 3, and is provided with three first insertion holes 3 for installing the first positioning devices 4, and the positions of the three first insertion holes match those of the sensors $Q_1$, $Q_2$ and $Q_3$. The three sensors $Q_1$, $Q_2$ and $Q_3$ obtain their coordinate information, which is then recorded and provided as the coordinate information of the first probe 11. Since the three sensors are located at the position points of the first probe 11, the coordinate information of the first probe 11 can be obtained by them.

The ultrasound unit 1 also includes a second probe 12 for monitoring the puncturing process. The second probe 12 is in communication connection with the processing and display unit 3, and the image scanned by the second probe 12 is displayed by the processing and display unit 3. The second probe 12 is a transesophageal ultrasound probe, and the second probe 12 can be a conventional ultrasound probe. For example, the second probe 12 can be Philips X7-2T. The second probe 12 provides real-time monitoring and evaluation for the puncturing, which further ensures the safety of intracardiac intervention.

The puncture needle unit 2 includes a puncture needle, and a plurality of second positioning devices 5 for providing coordinate information of the puncture needle are provided on the puncture needle. The coordinate information of the puncture needle includes the coordinate information of the position points on the puncture needle. The position points are selected to facilitate the determination of the position of the axis of the puncture needle. In one embodiment, the puncture needle is provided with two second positioning devices 5, and the two second positioning devices 5 are located at different positions on the axis of the puncture needle. This arrangement is for determining the axis of the puncture needle through the second positioning devices 5. The second positioning devices 5 are selected from sensors. Normally, the sensors are used in conjunction with a magnetic source and a magnetic locator, and the magnetic source and sensor are respectively connected to the magnetic locator. When in use, the magnetic source is located near the operating table. In one embodiment, 3DGuidance trakSTAR can be used. 3DGuidance trakSTAR includes the sensor, magnetic source and magnetic locator used in the present disclosure. Further, for the installation stability of the puncture needle and the second positioning devices 5, the puncture needle is provided with a puncture needle clamp 7, matched with the puncture needle. As shown in FIG. 4, the puncture needle clamp 7 is provided with two second insertion holes for installing the second positioning device 5, and the positions of the two second insertion holes match those of sensors B1 and B2. It can be seen from the above that the two sensors B1 and B2 can obtain and record their own coordinate information, which is then provided as the coordinate information of the puncture needle. Since the two sensors B1 and B2 are located on the puncture needle at multiple locations, the coordinate information of the puncture needle can be obtained.

The processing and display unit 3 includes at least a processor and a display. The processor may be a server or a general-purpose processor, including a central processing unit (CPU), and a network processor (NP). It can also be a Digital Signal Processing (DSP), Application Specific Integrated Circuit (ASIC), Field-Programmable Gate Array (Field-Programmable Gate Array, FPGA), other programming logic devices, discrete gates or transistor logic devices, or discrete hardware components. The processor is respectively in communication connection with the ultrasound unit 1, each of the first positioning devices 4, and each of the second positioning devices 5. The processor is communicatively connected to the display for display. More specifically, the processor is communicatively connected to the first probe 11 and the second probe 12.

More specifically, the processing and display unit 3, together with one or more other components, forms:

a first data acquisition unit, used to acquire the ultrasound image of the lesion and display it in the virtual coordinate system, and used to acquire the coordinate information of the first probe 11 when the latter is acquiring the ultrasound image of the lesion and display the coordinate information of the first probe 11 in the virtual coordinate system;

a planned path determination unit, used to determine the planned path L1 in the virtual coordinate system;

a second data acquisition unit, used to acquire the coordinate information of the second positioning devices 5 on the puncture needle in the virtual coordinate system and display the axis L2 of the virtual puncture needle and the vertex C2 of the virtual puncture needle; and a comparison unit, used to compare the axis L2 of the virtual puncture needle and the planned path L1 in the virtual coordinate system to see if they are coincident.

The first data acquisition unit includes at least: a first memory unit for storing the ultrasound image of the lesion, a second memory unit for storing the coordinate information of the first probe 11, the first positioning devices 4 on the first probe 11, the processor, and the first probe 11. The first memory unit and the second memory unit are electronically connected to the processor. The first probe 11 is in data communication with the processor, and produces the ultrasound image of the lesion. The first probe 11 sends data representing the ultrasound image of the lesion to the processor, and then processor stores the data representing the ultrasound image of the lesion on the first memory unit. The first positioning devices 4 are also in data communication with the processor, and send the coordinate information of the first probe 11 to the processor, which then stores the coordinate information of the first probe 11 on the second memory unit.

More specifically, in the first data acquisition unit, the ultrasound image of the lesion is obtained by scanning the lesion by the first probe 11.

The position of the ultrasound image of the lesion as displayed in the virtual coordinate system is not limited, and the selection of the origin of the virtual coordinate system is not limited. In order to facilitate data processing, in one embodiment, the ultrasound image of the lesion is fan-shaped, i.e. a sector, and the vertex C1 of the sector serves as the origin of the virtual coordinate system.

The first probe 11 can provide its own coordinate information through the first positioning devices 4. The coordinate information of the first positioning devices 4 is part of the coordinate information of a virtual first probe. The position of each first positioning device 4 in the virtual coordinate system can be used to represent the first probe 11 in the virtual coordinate system as the virtual first probe. In order to obtain the planned path more conveniently, the position of the axis of the first probe 11 in the virtual coordinate system needs to be determined first. In one embodiment, the first positioning devices 4 of the first probe 11 are all provided on a plane that coincides with the axis of the first probe 11 so that it is convenient to determine the coordinate information of the axis of the first probe 11. In the first probe 11 as shown in FIG. 2, the positions of the three sensors $Q_1$, $Q_2$ and $Q_3$ in the virtual coordinate system can be represented as the position of the first probe 11 in the virtual coordinate system, i.e., the virtual first probe. The axis of the first probe 11 lies in the plane containing Points $Q_1$, $Q_2$ and $Q_3$, and bisects Line Segment $Q_1$-$Q_2$.

In order to facilitate subsequent steps for determining the planned path, in one embodiment, the point of the lesion to be puncture at and sampled from (hereinafter, the puncture sampling point) can be positioned on the axis of the fan-shaped ultrasound image of the lesion.

In the planed path determination unit, according to the coordinate information of the first probe 11 in the virtual coordinate system, the position of the axis of the first probe 11 as projected onto the plane containing the fan-shaped ultrasound image of the lesion can be obtained by planar matrix conversion, so as to determine the planned path L1.

The planed path determination unit includes at least the first memory unit, which contains the ultrasound image of the lesion, the second memory unit, which contains the coordinate information of the first probe 11, a third memory unit, which contains algorithms for positioning the axis of the first probe 11 as projected onto the plane containing the ultrasound image of the lesion, and the processor. The processor is electrically connected to the first memory unit, the second memory unit, and the third memory unit. The processor retrieves data from the memory units, and calculates the axis of the first probe 11 as projected onto the plane containing the ultrasound image of the lesion, by applying the algorithms to the data stored on the first memory unit and the second memory unit. The algorithms include at least the transformation formula I as described below.

The ultrasound image of the lesion is fan-shaped in some embodiments. In general, the line passing through the apex of the fan-shaped ultrasound image of the lesion and the puncture sampling point of the lesion can serve as the actual planed path. When the puncture sampling point is on the axis of the fan-shaped ultrasound image of the lesion, the axis of the fan-shaped ultrasound image of the lesion can be used as the actual planned path. In the real world, the axis of the first probe 11 and the fan-shaped ultrasound image of the lesion should be on the same plane, the apexes of the first probe 11 and the fan-shaped ultrasound image of the lesion coincide, and the axis of the first probe 11 and the axis of the fan-shaped ultrasound image of the lesion coincide. Therefore, the planned path can be determined as soon as the position of the axis of the first probe 11 is determined.

However, the relative positions of the fan-shaped ultrasound image of the lesion and the axis of the first probe 11 in the virtual coordinate system do not match the actual relative positions of the two, so it is needed to project the axis of the first probe 11 onto the plane containing the fan-shaped ultrasound image of the lesion in the virtual coordinate system by conversion.

Specifically, the following transformation formula I may be used to perform planar matrix conversion, and obtain the transformed coordinate information of the projection of the axis of the first probe 11 onto the plane containing the ultrasound image of the lesion:

$$(x', y', z', 1) = T(x, y, z, 1)^T.$$

$(x', y', z')^T$ is the transformed coordinate information, and $(x, y, z)^T$ is the coordinate information before the transformation.

$T = T_4 T_3 T_1$, wherein T is the transformation matrix corresponding to the projection of the axis of the virtual first probe onto the plane containing the fan-shaped ultrasound image of the lesion in the virtual coordinate system.

$$T_4 = \begin{bmatrix} 1 & 0 & 0 & d_x \\ 0 & 1 & 0 & d_y \\ 0 & 0 & 1 & d_z \\ 0 & 0 & 0 & 1 \end{bmatrix},$$

$$\vec{d} = \left(-\overrightarrow{P_1 Q_1'} \cdot \vec{n_1}\right)\vec{n_1}, \vec{d} = (d_x, d_z, d_z), Q_1' = T_3 T_2 T_1 Q_1,$$

$$T_3 = \begin{bmatrix} 1 & 0 & 0 & q_x^1 \\ 0 & 1 & 0 & q_y^1 \\ 0 & 0 & 1 & q_z^1 \\ 0 & 0 & 0 & 1 \end{bmatrix},$$

$$T_2 = \begin{bmatrix} 1 & 0 & 0 & 0 \\ 0 & \cos\theta_x^1 & \sin\theta_x^1 & 0 \\ 0 & -\sin\theta_x^1 & \cos\theta_x^1 & 0 \\ 0 & 0 & 0 & 1 \end{bmatrix} \begin{bmatrix} \cos\theta_y^1 & 0 & \sin\theta_y^1 & 0 \\ 0 & 1 & 0 & 0 \\ -\sin\theta_y^1 & 0 & \cos\theta_y^1 & 0 \\ 0 & 0 & 0 & 1 \end{bmatrix} \begin{bmatrix} \cos\theta_y^2 & 0 & -\sin\theta_y^2 & 0 \\ 0 & 1 & 0 & 0 \\ \sin\theta_y^2 & 0 & \cos\theta_y^2 & 0 \\ 0 & 0 & 0 & 1 \end{bmatrix}$$

$$\begin{bmatrix} 1 & 0 & 0 & 0 \\ 0 & \cos\theta_x^2 & -\sin\theta_x^2 & 0 \\ 0 & \sin\theta_x^2 & \cos\theta_x^2 & 0 \\ 0 & 0 & 0 & 1 \end{bmatrix},$$

$$\cos\theta_x^2 = \frac{n_z^2}{\sqrt{(n_y^2)^2 + (n_z^2)^2}}, \sin\theta_x^2 = \frac{n_y^2}{\sqrt{(n_y^2)^2 + (n_z^2)^2}},$$

$$\cos\theta_y^2 = \frac{\sqrt{(n_y^2)^2 + (n_z^2)^2}}{\sqrt{(n_x^2)^2 + (n_y^2)^2 + (n_z^2)^2}}, \sin\theta_y^2 = \frac{n_x^2}{\sqrt{(n_x^2)^2 + (n_y^2)^2 + (n_z^2)^2}},$$

$$\cos\theta_x^1 = \frac{n_z^1}{\sqrt{(n_y^1)^2 + (n_z^1)^2}}, \sin\theta_x^1 = \frac{n_y^1}{\sqrt{(n_y^1)^2 + (n_z^1)^2}},$$

$$\cos\theta_y^1 = \frac{\sqrt{(n_y^1)^2 + (n_z^1)^2}}{\sqrt{(n_x^1)^2 + (n_y^1)^2 + (n_z^1)^2}}, \sin\theta_y^1 = \frac{n_x^1}{\sqrt{(n_x^1)^2 + (n_y^1)^2 + (n_z^1)^2}},$$

$$\vec{n_1} = (n_x^1, n_y^1, n_z^1), \vec{n_2} = (n_x^2, n_y^2, n_z^2),$$

$$\vec{n_1} = \frac{\overrightarrow{P_1 P_2} \times \overrightarrow{P_1 P_3}}{|\overrightarrow{P_1 P_2}||\overrightarrow{P_1 P_3}|}, \vec{n_2} = \frac{\overrightarrow{Q_1 Q_2} \times \overrightarrow{Q_1 Q_3}}{|\overrightarrow{Q_1 Q_2}||\overrightarrow{Q_1 Q_3}|},$$

$$T_1 = \begin{bmatrix} 1 & 0 & 0 & -q_x^1 \\ 0 & 1 & 0 & -q_y^1 \\ 0 & 0 & 1 & -q_z^1 \\ 0 & 0 & 0 & 1 \end{bmatrix}.$$

$P_1$, $P_2$, $P_3$ are three non-collinear sampling points on the plane $F_1$ containing the fan-shaped ultrasound image of the lesion, and $Q_1$, $Q_2$, $Q_3$ are three non-collinear points on the plane $F_2$ containing the axis of a virtual first probe, $P_1(p_x^1, p_y^1, p_z^1)$, $P_2(p_x^2, p_y^2, p_z^2)$, $P_3(p_x^3, p_y^3, p_z^3)$, $Q_1(q_x^1, q_y^1, q_z^1)$, $Q_2(q_x^2, q_y^2, q_z^2)$, $Q_3(q_x^3, q_y^3, q_z^3)$ are the coordinates of $P_1$, $P_2$, $P_3$, $Q_1$, $Q_2$, and $Q_3$ respectively. Their positions may be fixed relative to the plane they are on. That is, their coordinates relative to the origin may change when the planes undergo transformations.

$\vec{n}_1$ is a unit normal vector of plane $F_1$, and $\vec{n}_2$ is a unit normal vector of the plane $F_2$.

The plane $F_2$ is translated until $Q_1$ coincides with the origin of the virtual coordinate system, thereby obtaining the plane $F_2'$. Then the unit normal vector of the plane $F_2'$ is rotated around the origin until it coincides with the unit normal vector $\vec{n}_1$ of the plane $F_1$, the angle at which the unit normal vector of the plane $F_2'$ has rotated counterclockwise around the x axis accordingly is $\theta_x^2$ or $2\pi - \theta_x^1$, and the angle at which the unit normal vector of the plane $F_2'$ has rotated counterclockwise around the y axis accordingly is $\theta_y^1$ or $2\pi - \theta_y^2$.

The second data acquisition unit at least includes the second positioning devices 5 on the puncture needle, the display, the processor, and a fourth memory unit for storing the coordinate information provided by the second positioning devices 5. The processor is electrically connected to the fourth memory unit and the display, calculates the axis L2 of the virtual puncture needle and the vertex C2 of the virtual puncture needle at least partially based on the coordinate information stored on the fourth memory unit, and transmits data representing the axis L2 and the vertex C2 to the display, which emits light mimicking the axis L2 and the vertex C2.

The comparison unit at least includes a fifth memory unit, which contains data presenting the axis L2 of the virtual puncture needle calculated by the processor, and data presenting the axis of the first probe 11, and the processor. The processor is electrically connected to the fifth memory unit, and compares the coordinate information of the axis L2 of the virtual puncture needle and the axis of the first probe 11. The comparison unit may also include the display. When the processor finds that the axis of the first probe 11 and the axis L2 of the virtual puncture needle coincide, the processor sends a signal presenting a judgment of coincidence to the display, then the display may indicate the judgment of coincidence to the user, for example, by emitting light mimicking a check mark, or by emitting green light. The first memory unit, second memory unit, third memory unit, fourth memory unit, and the fifth memory unit are included in the processing and display unit (3)

The present disclosure also provides a planar matrix conversion device for projecting the axis of the first probe 11 onto the plane containing the fan-shaped ultrasound image of the lesion, which includes:

a sampling unit, used to obtain the coordinates of three non-collinear sampling points on a virtual plane $F_1$ containing the fan-shaped ultrasound image of the lesion in a virtual coordinate system $P_1(p_x^1, p_y^1, p_z^1)$, $P_2(p_x^2, p_y^2, p_z^2)$, $P_3(p_x^3, p_y^3, p_z^3)$, and the coordinates of three non-collinear sampling points on the plane $F_2$ containing the axis of the virtual first probe $Q_1(q_x^1, q_y^1, q_z^1)$, $Q_2(q_x^2, q_y^2, q_z^2)$, $Q_3(q_x^3, q_y^3, q_z^3)$;

a first translation unit, used to obtain a transformation matrix $T_1$ corresponding to the transformation from the plane $F_2$ to a plane $F_2'$, wherein the plane $F_2'$ is obtained by translating the plane $F_2$ until any sampling point on $F_2$ is coincident with the origin of the virtual coordinate system;

a rotation unit, used to obtain a transformation matrix $T_2$ corresponding to the transformation from the plane $F_2'$ to a plane $F_2''$, wherein the plane $F_2''$ is obtained by rotating the plane $F_2'$ around the origin of the coordinate system until its unit normal vector coincides with the unit normal vector $\vec{n}_1$ of the plane $F_1$;

a second translation unit, used to obtain a transformation matrix $T_3$ corresponding to the transformation from the plane $F_2''$ to a plane $F_2'''$, wherein the $F_2'''$ is obtained by translating the plane $F_2''$ until the sampling point coincident with is the origin of the coordinate system in the first translation unit returns to its initial position;

a third translation unit, used to obtain a transformation matrix $T_4$ corresponding to the transformation from the plane $F_2'''$ to a plane $F_2''''$, wherein the plane $F_2''''$ is obtained by first obtaining the distance between the plane $F_2'''$ and the plane $F_1$, and then translating the plane $F_2'''$ along its unit normal vector by a corresponding vector d to coincide with the plane $F_1$, wherein the coordinates of the projection of the axis of the ultrasound probe onto the plane $F_1$ can be obtained by using a coordinate transformation formula and the coordinates of the axis of the ultrasound probe on the plane $F_2$.

Specifically, in the sampling unit, the plane $F_1$ is a virtual plane displayed in the virtual coordinate system, which contains an ultrasound image of the lesion, obtained by scanning the lesion with the first probe 11. The plane $F_2$ is the plane containing the axis of the first probe 11 as shown in the virtual coordinates system when the first probe 11 is scanning the lesion to obtain the ultrasound image of the lesion. The plane $F_2$ can be obtained according to the sensors on the first probe 11.

In one embodiment, the virtual coordinate system also displays the apex C1 of the fan-shaped ultrasound image of the lesion to assist in determining the puncture point. Specifically, the point where the first probe 11 is in contact with the patient's chest wall is represented in the virtual coordinate system as the apex C1 of the fan-shaped ultrasound image of the lesion.

In one embodiment, the axis of the first probe 11 and the plane $F_2$ can be determined according to the positions of the first positioning devices 4 on the first probe 11. In one embodiment, in order to facilitate said determination, the first positioning devices 4 are located on the axis of the first probe 11.

The first positioning devices 4 may be sensors, and three non-collinear sensors $Q_1$, $Q_2$ and $Q_3$ as shown in FIG. 2 are provided on the axis of the first probe 11 to locate the axis of the first probe 11 and the plane $F_2$.

The three non-collinear sensors $Q_1$, $Q_2$ and $Q_3$ constitute the vertices of a right triangle. This arrangement is for determining the axis of the first probe 11 by the first positioning devices 4. The axis of the first probe 11 lies in the plane containing Points $Q_1$, $Q_2$ and $Q_3$, and bisects Line Segment $Q_1$-$Q_2$.

In one embodiment, the virtual three-dimensional coordinate system uses the vertex C1 of the fan-shaped ultrasound image of the lesion as the origin of the coordinate system. The plane containing the fan-shaped ultrasound image of the lesion is $F_1$.

In another embodiment, in the first translation unit, the plane $F_2$ is translated until Point $Q_1$ coincides with the origin of the coordinate system.

The vertex C1 of the fan-shaped ultrasound image of the lesion is taken as the origin of the coordinate system, and the plane $F_2$ is translated until $Q_1$ coincides with the origin.

$$\begin{bmatrix} x' \\ y' \\ z' \\ x \end{bmatrix} = \begin{bmatrix} 1 & 0 & 0 & -q_x^1 \\ 0 & 1 & 0 & -q_y^1 \\ 0 & 0 & 1 & -q_z^1 \\ 0 & 0 & 0 & 1 \end{bmatrix} \begin{bmatrix} x \\ y \\ z \\ x \end{bmatrix},$$

wherein $$T_1 = \begin{bmatrix} 1 & 0 & 0 & -q_x^1 \\ 0 & 1 & 0 & -q_y^1 \\ 0 & 0 & 1 & -q_z^1 \\ 0 & 0 & 0 & 1 \end{bmatrix}.$$

The rotation unit is used to rotate the unit normal vector of the plane $F_2'$ around the origin of the coordinate system until the unit normal vector of the plane $F_2'$ coincides with the unit normal vector of the plane $F_1$ containing the fan-shaped ultrasound image of the lesion, in order to obtain the plane $F_2''$, the corresponding transformation matrix $T_2$ is:

$$T_2 = \begin{bmatrix} 1 & 0 & 0 & 0 \\ 0 & \cos\theta_x^1 & \sin\theta_x^1 & 0 \\ 0 & -\sin\theta_x^1 & \cos\theta_x^1 & 0 \\ 0 & 0 & 0 & 1 \end{bmatrix} \begin{bmatrix} \cos\theta_y^1 & 0 & \sin\theta_y^1 & 0 \\ 0 & 1 & 0 & 0 \\ -\sin\theta_y^1 & 0 & \cos\theta_y^1 & 0 \\ 0 & 0 & 0 & 1 \end{bmatrix} \begin{bmatrix} \cos\theta_y^2 & 0 & -\sin\theta_y^2 & 0 \\ 0 & 1 & 0 & 0 \\ \sin\theta_y^2 & 0 & \cos\theta_y^2 & 0 \\ 0 & 0 & 0 & 1 \end{bmatrix}$$

$$\begin{bmatrix} 1 & 0 & 0 & 0 \\ 0 & \cos\theta_x^2 & -\sin\theta_x^2 & 0 \\ 0 & \sin\theta_x^2 & \cos\theta_x^2 & 0 \\ 0 & 0 & 0 & 1 \end{bmatrix},$$

wherein $$\cos\theta_x^2 = \frac{n_z^2}{\sqrt{(n_y^2)^2 + (n_z^2)^2}}, \sin\theta_x^2 = \frac{n_y^2}{\sqrt{(n_y^2)^2 + (n_z^2)^2}},$$

$$\cos\theta_y^2 = \frac{\sqrt{(n_y^2)^2 + (n_z^2)^2}}{\sqrt{(n_x^2)^2 + (n_y^2)^2 + (n_z^2)^2}}, \sin\theta_y^2 = \frac{n_x^2}{\sqrt{(n_x^2)^2 + (n_y^2)^2 + (n_z^2)^2}},$$

$$\cos\theta_x^1 = \frac{n_z^1}{\sqrt{(n_y^1)^2 + (n_z^1)^2}}, \sin\theta_x^1 = \frac{n_y^1}{\sqrt{(n_y^1)^2 + (n_z^1)^2}}, \text{ and}$$

$$\cos\theta_y^1 = \frac{\sqrt{(n_y^1)^2 + (n_z^1)^2}}{\sqrt{(n_x^1)^2 + (n_y^1)^2 + (n_z^1)^2}}, \sin\theta_y^1 = \frac{n_x^1}{\sqrt{(n_x^1)^2 + (n_y^1)^2 + (n_z^1)^2}}.$$

The plane $F_2$ is translated until $Q_1$ coincides with the origin of the virtual coordinate system, thereby obtaining the plane $F_2'$. Then the unit normal vector of the plane $F_2'$ is rotated around the origin until it coincides with the unit normal vector $\vec{n}_1$ of the plane $F_1$, the angle at which the unit normal vector of the plane $F_2'$ has rotated counterclockwise around the x axis accordingly is $\theta_x^2$ or $2\pi-\theta_x^1$, and the angle at which the unit normal vector of the plane $F_2'$ has rotated counterclockwise around the y axis accordingly is $\theta_y^1$ or $2\pi-\theta_y^2$.

Through the rotation unit, the plane $F_2'$ can thus be rotated and transformed to obtain the plane $F_2''$.

The second translation unit is used to translate the plane $F_2''$ until the sampling point coincident with the origin of the coordinate system in the first translation unit returns to its initial position, in order to obtain the plane $F_2'''$. Taking the sampling point $Q_1$ as an example, the corresponding transformation matrix $T_3$ is given by:

$$\begin{bmatrix} x' \\ y' \\ z' \\ x \end{bmatrix} = T_3 \begin{bmatrix} x \\ y \\ z \\ x \end{bmatrix}, T_3 = \begin{bmatrix} 1 & 0 & 0 & q_x^1 \\ 0 & 1 & 0 & q_y^1 \\ 0 & 0 & 1 & q_z^1 \\ 0 & 0 & 0 & 1 \end{bmatrix}.$$

The third translation unit is used to obtain the distance d between the plane $F_2'''$ and the plane $F_1$. The vector representing the translation required for the plane $F_2'''$ to coincide with the plane $F_1$ is given by: $\vec{d} = (-\vec{P_1Q_1'} \cdot \vec{n_1})\vec{n_1}$, wherein $Q'_1 = T_3T_2T_1Q_1$, $$T_4 = \begin{bmatrix} 1 & 0 & 0 & d_x \\ 0 & 1 & 0 & d_y \\ 0 & 0 & 1 & d_z \\ 0 & 0 & 0 & 1 \end{bmatrix},$$

The plane $F_2'''$ translate along the vector $\vec{d}$ until it coincide with the plane $F_1$, thereby obtaining the plane $F_2''''$.

In summary, the final transformation matrix is given by $T = T_4T_3T_2T_1$.

For any point $(x, y, z)^T$ on the plane $F_2$, $(x', y', z', 1) = T(x, y, z, 1)^T$, wherein $(x', y', z')^T$ is the coordinate information after the transformation, and $(x, y, z)^T$ is the coordinate information before the transformation.

Thus points on the plane $F_1$ that correspond to the points on the plane $F_2$ can be found.

According to the above formulas, the points on the plane $F_1$ that correspond to the points $Q_1$, $Q_2$, and $Q_3$, which are on the plane $F_2$, can be found. So is the line that lies in the plane $F_2$ and bisects the Line Segment $Q_1$-$Q_2$. A path coincident with this line is the planned path L1 in the plane $F_1$.

In the second data acquisition unit, according to the coordinate information of the second positioning devices 5, the coordinate information of the axis L2 of the virtual puncture needle and the apex C2 of the virtual puncture needle as projected onto the plane $F_1$ is obtained (i.e., transformed coordinate information) through planar matrix conversion, and the axis L2 of the virtual puncture needle and the apex C2 of the virtual puncture needle are represented in the coordinate system based on the transformed coordinate information.

Specifically, in the coordinate system, when the apex C1 of the fan-shaped ultrasound image of the lesion is taken as the origin, the transformation formula I is used for planar matrix conversion to obtain the corresponding axis L2 of the virtual puncture needle and apex C2 of the virtual puncture needle.

The comparison unit is used in the virtual coordinate system to compare the apex C2 of the virtual puncture needle and the apex C1 of the fan-shaped ultrasound image of the lesion to see if they coincide, and compare the axis L2 of the virtual puncture needle and the planned path L1 to see if they coincide. When the apex C2 of the virtual puncture needle and the apex C1 of the fan-shaped ultrasound image of the lesion coincide, and the axis L2 of the virtual puncture needle and the planned path L1 coincide, a judgment of coincidence is returned. The judgment of coincidence may be required before any puncture procedure.

Figure 7:
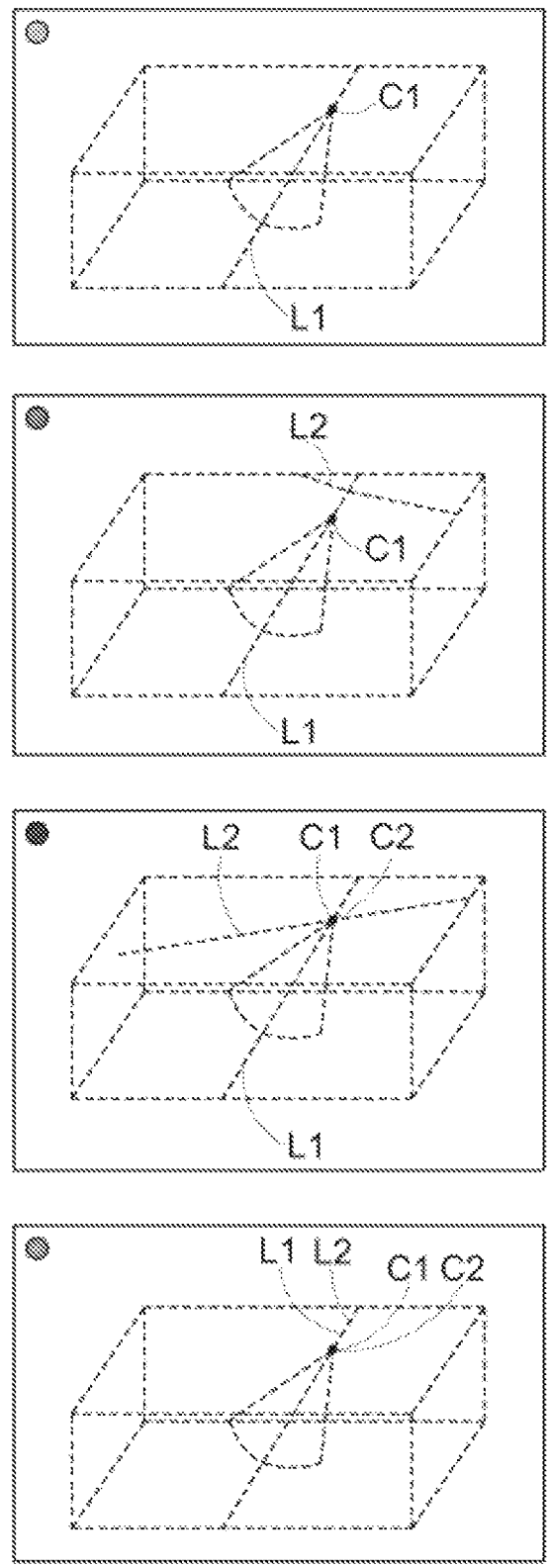
FIG. 7 is a schematic diagram showing visual interfaces of a puncture needle positioning system according to some embodiments of the present disclosure.
Figure 8:
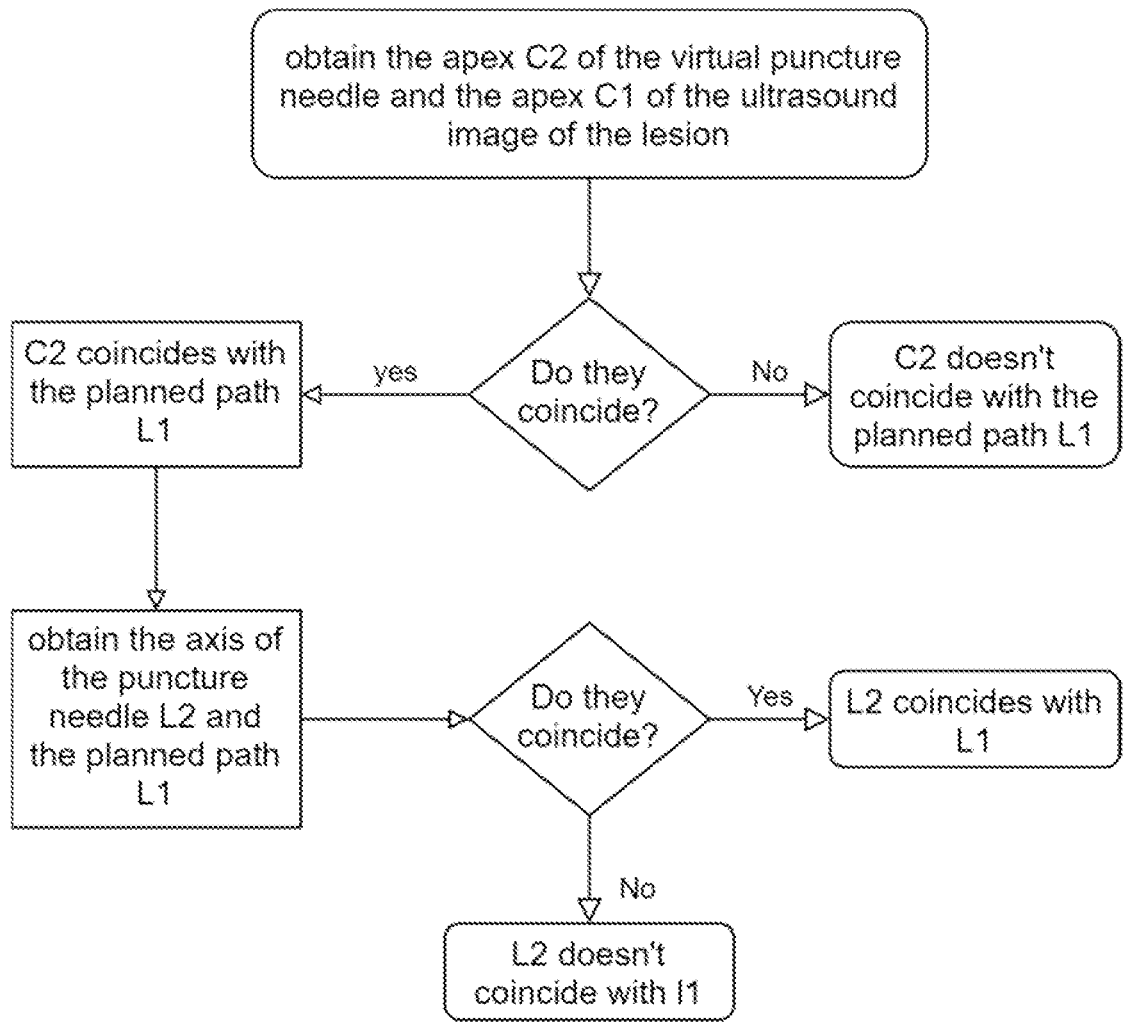
FIG. 8 is a flow chart illustrating steps of determining if a virtual puncture needle and a planned path coincide according to some embodiments of the present disclosure.

More specifically, as shown in FIG. 8, first, a determination is made as to whether the apex C2 of the virtual puncture needle and the apex C1 of the fan-shaped ultrasound image of the lesion coincide; if not, then a judgment of "no coincidence" is returned; if yes, then another determination is made as to whether the axis L2 of the virtual puncture needle and the planed path L1 coincide. If the axis L2 of the virtual puncture needle and the planed path L1 coincide, then a judgment of coincidence is returned, and otherwise a judgment of "no coincidence" is returned. Corresponding signals indicating coincidence or the lack of it may be given. In one embodiment, the apex C2 of the virtual puncture needle serves as the axis to for the puncture needle to adjust its orientation, as shown in FIG. 7. Initially, the system's indicator light is red, and when the apex C2 of the virtual puncture needle and the apex C1 of the fan-shaped ultrasound image of the lesion coincide, the indicator light turns blue; when the axis L2 of the puncture needle coincides with the planned path L1, the indicator light turns green. The medical staff monitors information related to the coincidence or the lack of it of the central axis L2 of the puncture needle and the planned path L1, and adjusts the puncture needle according to the color of the indicator light, which may be displayed on a virtual interface, during the movement of the puncture needle to assist the puncture procedure. The path suggested by a green indicator light is adopted to perform the puncturing.

Based on the transformation formula, a set of coordinate information can only correspond to one set of transformed coordinate information.

Similarly, there is only one line in the space whose transformed coordinate information corresponds to the axis of the fan-shaped ultrasound image of the lesion. Only when the axis of the puncture needle coincides with this line, can the corresponding axis of the virtual puncture needle coincide with the axis of the fan-shaped ultrasound image of the lesion (i.e., the planned path L1); when the axis of the puncture needle does not coincide with this line, the axis of the virtual puncture needle does not coincide with the planned path L1.

The working process of the puncture needle positioning system of the present disclosure:

The first probe 11 provided with the first positioning devices 4 scans the lesion to obtain an ultrasound image of the lesion, and the ultrasound image of the lesion and the first probe 11 are displayed in the virtual coordinate system of the processing and display unit 3. The ultrasound image of the lesion shows the fan-shaped area scanned by the first probe 11. The apex C1 of the fan-shaped ultrasound image of the lesion corresponds to the contact point between the first probe and the patient's skin, and this contact point is used as the point where the chest wall is to be punctured (i.e., chest wall puncture point). The plane containing the axis of the first probe 11 is transformed to coincide with the plane containing the ultrasound image of the lesion through a coordinate transformation formula, in order to obtain the planned path L1. The apex of the puncture needle is placed at the chest wall puncture point. The coordinate information of the puncture needle provided by the second positioning devices 5 are recorded, and the axis L2 of the puncture needle is displayed in the virtual coordinate system. The orientation of the puncture needle is adjusted with the chest wall puncture point as the center of rotation until the system indicates that the axis L2 of the virtual puncture needle and the planned path L1 coincide, and the puncture needle is then maintained at the position for the puncturing procedure.

In one embodiment, during the puncturing procedure, the system can indicate in real time whether the axis of the puncture needle coincides with the planned path L1, and ensure the procedure is carried out smoothly while monitored by the second probe 12.

The present disclosure also provides a positioning method for a puncture needle, comprising:

S100 acquiring the ultrasound image of the lesion and displaying it in the virtual coordinate system; acquiring the coordinate information of a first probe 11 when the latter is acquiring the ultrasound image of the lesion and displaying the first probe 11 in the virtual coordinate system, wherein the first probe 11 obtains the ultrasound image by directing sound waves at the lesion and receiving sound waves reflected back from the lesion thereby obtaining data representing the ultrasound image of the lesion;

S200 determining a planned path L1 in the virtual coordinate system;

S300 obtaining the coordinate information of second positioning devices 5 on a puncture needle in the virtual coordinate system and displaying the axis L2 of the virtual puncture needle and the apex C2 of the virtual puncture needle;

S400 comparing the axis L2 of the virtual puncture needle with the planned path L1 in the virtual coordinate system to see if they coincide.

Specifically, at S100, the ultrasound image of the lesion is obtained by scanning the lesion by the first probe 11.

The position of the ultrasound image of the lesion as displayed in the virtual coordinate system is not limited, and the selection of the origin of the virtual coordinate system is not limited. In order to facilitate data processing, in one embodiment, the ultrasound image of the lesion is fan-shaped, i.e. a sector, and the vertex C1 of the fan-shaped ultrasound image of the lesion serves as the origin of the virtual coordinate system.

The first probe 11 can provide its own coordinate information through the first positioning devices 4. The coordinate information of the first positioning devices 4 is part of the coordinate information of a virtual first probe. The position of each first positioning device 4 in the virtual coordinate system can be used to represent the first probe 11 in the virtual coordinate system as the virtual first probe. In order to obtain the planned path more conveniently, the position of the axis of the first probe 11 in the virtual coordinate system needs to be determined first. In one embodiment, the first positioning devices 4 of the first probe 11 are all provided on a plane that coincides with the axis of the first probe 11 so that it is convenient to determine the coordinate information of the axis of the first probe 11. In the first probe 11 as shown in FIG. 2, the positions of the three sensors $Q_1$, $Q_2$ and $Q_3$ in the virtual coordinate system can be represented as the position of the first probe 11 in the virtual coordinate system, i.e., the virtual first probe. The axis of the first probe 11 lies in the plane containing Points $Q_1$, $Q_2$ and $Q_3$, and bisects Line Segment $Q_1$-$Q_2$ In order to facilitate subsequent steps for determining the planned path, in one embodiment, the point of the lesion to be punctured at and sampled from (hereinafter, the puncture sampling point) can be positioned on the axis of the fan-shaped ultrasound image of the lesion.

At S200, according to the coordinate information of the first probe 11 in the virtual coordinate system, the position of the axis of the first probe 11 as projected to the plane containing the fan-shaped ultrasound image of the lesion can be obtained by planar matrix conversion, so as to determine the planned path L1.

The ultrasound image of the lesion is fan-shaped in some embodiments. In general, the line passing through the apex of the fan-shaped ultrasound image of the lesion and the puncture sampling point of the lesion can serve as the actual planed path. When the puncture sampling point is on the axis of the fan-shaped ultrasound image of the lesion, the axis of the fan-shaped ultrasound image of the lesion can be used as the actual planned path. In the real world, the axis of the first probe 11 and the fan-shaped ultrasound image of the lesion should be on the same plane, the apexes of the first probe 11 and the fan-shaped ultrasound image of the lesion, and the axis of the first probe 11 and the axis of the fan-shaped ultrasound image of the lesion coincide. Therefore, the planned path can be determined as soon as the position of the axis of the first probe 11 is determined.

However, the relative positions of the fan-shaped ultrasound image of the lesion and the axis of the first probe 11 in the virtual coordinate system do not match the actual relative positions of the two, so it is needed to project the axis of the first probe 11 to the plane containing the fan-shaped ultrasound image of the lesion in the virtual coordinate system by conversion.

Specifically, the following transformation formula I may be used to perform planar matrix conversion, and obtain the transformed coordinate information of the projection of the axis of the first probe 11 onto the ultrasound image of the lesion:

$$(x',y',z',1)=T(x,y,z,1)^T.$$

$(x', y', z')^T$ is the transformed coordinate information, and $(x, y, z)^T$ is the coordinate information before the transformation.

$T=T_4 T_3 T_2 T_1$, wherein T is the transformation matrix corresponding to the projection of the axis of the virtual first probe onto the plane containing the fan-shaped ultrasound image of the lesion in the virtual coordinate system.

$$T_4 = \begin{bmatrix} 1 & 0 & 0 & d_x \\ 0 & 1 & 0 & d_y \\ 0 & 0 & 1 & d_z \\ 0 & 0 & 0 & 1 \end{bmatrix},$$

$\vec{d} = \left(-\overrightarrow{P_1 Q_1'} \cdot \vec{m_1}\right)\vec{m_1}$, $\vec{d} = (d_x, d_z, d_z)$, $Q_1' = T_3 T_2 T_1 Q_1$, $$T_3 = \begin{bmatrix} 1 & 0 & 0 & q_x^1 \\ 0 & 1 & 0 & q_y^1 \\ 0 & 0 & 1 & q_z^1 \\ 0 & 0 & 0 & 1 \end{bmatrix},$$

$$T_2 = \begin{bmatrix} 1 & 0 & 0 & 0 \\ 0 & \cos\theta_x^1 & \sin\theta_x^1 & 0 \\ 0 & -\sin\theta_x^1 & \cos\theta_x^1 & 0 \\ 0 & 0 & 0 & 1 \end{bmatrix} \begin{bmatrix} \cos\theta_y^1 & 0 & \sin\theta_y^1 & 0 \\ 0 & 1 & 0 & 0 \\ -\sin\theta_y^1 & 0 & \cos\theta_y^1 & 0 \\ 0 & 0 & 0 & 1 \end{bmatrix} \begin{bmatrix} \cos\theta_y^2 & 0 & -\sin\theta_y^2 & 0 \\ 0 & 1 & 0 & 0 \\ \sin\theta_y^2 & 0 & \cos\theta_y^2 & 0 \\ 0 & 0 & 0 & 1 \end{bmatrix}$$

-continued $$\begin{bmatrix} 1 & 0 & 0 & 0 \\ 0 & \cos\theta_x^2 & -\sin\theta_x^2 & 0 \\ 0 & \sin\theta_x^2 & \cos\theta_x^2 & 0 \\ 0 & 0 & 0 & 1 \end{bmatrix},$$

$$\cos\theta_x^2 = \frac{n_z^2}{\sqrt{(n_y^2)^2 + (n_z^2)^2}}, \sin\theta_x^2 = \frac{n_y^2}{\sqrt{(n_y^2)^2 + (n_z^2)^2}},$$

$$\cos\theta_y^2 = \frac{\sqrt{(n_y^2)^2 + (n_z^2)^2}}{\sqrt{(n_x^2)^2 + (n_y^2)^2 + (n_z^2)^2}}, \sin\theta_y^2 = \frac{n_x^2}{\sqrt{(n_x^2)^2 + (n_y^2)^2 + (n_z^2)^2}},$$

$$\cos\theta_x^1 = \frac{n_z^1}{\sqrt{(n_y^1)^2 + (n_z^1)^2}}, \sin\theta_x^1 = \frac{n_y^1}{\sqrt{(n_y^1)^2 + (n_z^1)^2}},$$

$$\cos\theta_y^1 = \frac{\sqrt{(n_y^1)^2 + (n_z^1)^2}}{\sqrt{(n_x^1)^2 + (n_y^1)^2 + (n_z^1)^2}}, \sin\theta_y^1 = \frac{n_x^1}{\sqrt{(n_x^1)^2 + (n_y^1)^2 + (n_z^1)^2}},$$

$$\vec{n_1} = \frac{\vec{P_1P_2} \times \vec{P_1P_3}}{|\vec{P_1P_2}||\vec{P_1P_3}|}, \vec{n_2} = \frac{\vec{Q_1Q_2} \times \vec{Q_1Q_3}}{|\vec{Q_1Q_2}||\vec{Q_1Q_3}|},$$

$$\vec{n_1} = (n_x^1, n_y^1, n_z^1), \vec{n_2} = (n_x^2, n_y^2, n_z^2),$$

$$T_1 = \begin{bmatrix} 1 & 0 & 0 & -q_x^1 \\ 0 & 1 & 0 & -q_y^1 \\ 0 & 0 & 1 & -q_z^1 \\ 0 & 0 & 0 & 1 \end{bmatrix}.$$

$P_1$, $P_2$, $P_3$ are three non-collinear sampling points on the plane $F_1$ containing the fan-shaped ultrasound image of the lesion, and $Q_1$, $Q_2$, $Q_3$ are three non-collinear points on an a plane containing the axis of a virtual first probe, $P_1(p_x^1, p_y^1, p_z^1)$, $P_2(p_x^2, p_y^2, p_z^2)$, $P_3(p_x^3, p_y^3, p_z^3)$, $Q_1(q_x^1, q_y^1, q_z^1)$, $Q_2(q_x^2, q_y^2, q_z^2)$, $Q_3(q_x^3, q_y^3, q_z^3)$ are the coordinates of $P_1$, $P_2$, $P_3$, $Q_1$, $Q_2$, and $Q_3$ respectively. Their positions may be fixed relative to the plane they are on. That is, their coordinates may change when the planes undergo transformations.

$\vec{n}_1$ is a unit normal vector of the plane $F_1$, and $\vec{n}_2$ is a unit normal vector of the plane $F_2$.

The plane $F_2$ is translated until $Q_1$ coincides with the origin of the virtual coordinate system, thereby obtaining the plane $F_2'$. Then the unit normal vector of the plane $F_2'$ is rotated around the origin until it coincides with the unit normal vector $\vec{n}_1$ of the plane $F_1$; the angle at which the unit normal vector of the plane $F_2'$ has rotated counterclockwise around the x axis accordingly is $\theta_x^2$ or $2\pi - \theta_x^1$, and the angle at which the unit normal vector of the plane $F_2'$ has rotated counterclockwise around the y axis accordingly is $\theta_y^1$ or $2\pi - \theta_y^2$.

Figure 6:
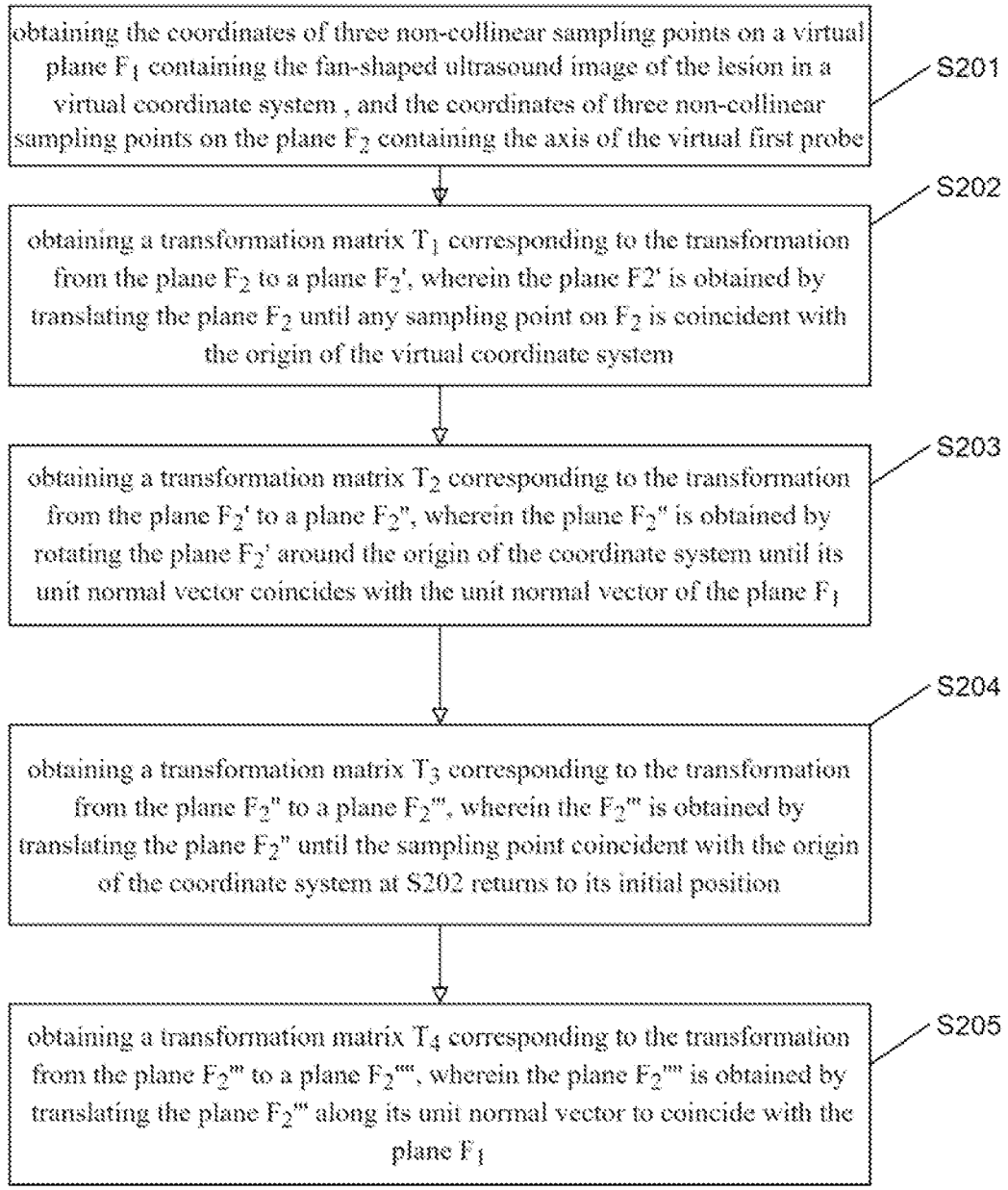
FIG. 6 is a flow chart illustrating a method for converting coordinates when projecting the axis of a first probe onto an ultrasound image according to some embodiments of the present disclosure.

As shown in FIG. 6, the process of obtaining coordinate transformation formulas corresponding to the transformation of projecting the axis of the first probe 11 onto the plane containing the ultrasound image of the lesion is as follows:

S201 obtaining the coordinates of three non-collinear sampling points on a virtual plane $F_1$ containing the fan-shaped ultrasound image of the lesion in a virtual coordinate system $P_1(p_x^1, p_y^1, p_z^1)$, $P_2(p_x^2, p_y^2, p_z^2)$, $P_3(p_x^3, p_y^3, p_z^3)$, and the coordinates of three non-collinear sampling points on the plane $F_2$ containing the axis of the virtual first probe $Q_1(q_x^1, q_y^1, q_z^1)$, $Q_2(q_x^2, q_y^2, q_z^2)$, $Q_3(q_x^3, q_y^3, q_z^3)$;

S202 obtaining a transformation matrix $T_1$ corresponding to the transformation from the plane $F_2$ to a plane $F_2'$, wherein the plane $F_2'$ is obtained by translating the plane $F_2$ until any sampling point on $F_2$ is coincident with the origin of the virtual coordinate system;

S203 obtaining a transformation matrix $T_2$ corresponding to the transformation from the plane $F_2'$ to a plane $F_2''$, wherein the plane $F_2''$ is obtained by rotating the plane $F_2'$ around the origin of the coordinate system until its unit normal vector coincides with the unit normal vector of the plane $F_1$;

S204 obtaining a transformation matrix $T_3$ corresponding to the transformation from the plane $F_2''$ to a plane $F_2'''$, wherein the $F_2'''$ is obtained by translating the plane $F_2''$ until the sampling point coincident with the origin of the coordinate system at S202 returns to its initial position;

S205 obtaining a transformation matrix $T_4$ corresponding to the transformation from the plane $F_2'''$ to a plane $F_2''''$, wherein the plane $F_2''''$ is obtained by first obtaining the distance between the plane $F_2'''$ and the plane $F_1$, and then translating the plane $F_2'''$ along its unit normal vector by a corresponding vector $\vec{d}$ to coincide with the plane $F_1$, wherein the coordinates of the projection of the axis of the ultrasound probe onto the plane $F_1$ can be obtained by using a coordinate transformation formula and the coordinates of the axis of the ultrasound probe on the plane $F_2$.

Specifically, at S201, the plane $F_1$ is a virtual plane displayed in the virtual coordinate system, which contains an ultrasound image of the lesion, obtained by scanning the lesion with the first probe 11. The plane $F_2$ is the plane containing the axis of the first probe 11 as shown in the virtual coordinates system when the first probe 11 is scanning the lesion to obtain the ultrasound image of the lesion. The plane $F_2$ can be located according to the sensors on the first probe 11.

In one embodiment, the virtual coordinate system also displays the apex C1 of the fan-shaped ultrasound image of the lesion to assist in determining the puncture point. Specifically, the point where the first probe 11 is in contact with the patient's chest wall is represented in the virtual coordinate system as the apex C1 of the fan-shaped ultrasound image of the lesion.

In one embodiment, the axis and plane containing the axis of the first probe 11 can be determined according to the positions of the first positioning devices 4 on the first probe 11. In one embodiment, in order to facilitate said determination, the first positioning devices 4 are located on the axis of the first probe 11.

The first positioning devices 4 may be sensors, and three non-collinear sensors $Q_1$, $Q_2$ and $Q_3$ as shown in FIG. 2 are provided on the axis of the first probe 11 to locate the axis and plane containing the axis of the first probe 11.

The three non-collinear sensors $Q_1$, $Q_2$ and $Q_3$ constitute the vertices of a right triangle. This arrangement is for determining the axis of the first probe 11 by the first positioning devices 4. The axis of the first probe 11 lies in the plane containing Points $Q_1$, $Q_2$ and $Q_3$, and bisects Line Segment $Q_1$-$Q_2$.

In one embodiment, the virtual three-dimensional coordinate system uses the vertex C1 of the fan-shaped ultrasound image of the lesion as the origin of the coordinate system. The plane containing the fan-shaped ultrasound image of the lesion is $F_1$.

In another embodiment, at S202, the plane $F_2$ is translated until Point $Q_1$ coincides with the origin of the coordinate system.

In one embodiment, the vertex C1 of the fan-shaped ultrasound image of the lesion is taken as the origin of the coordinate system, and the plane $F_2$ is translated until $Q_1$ coincides with the origin.

The corresponding coordinate transformation is given by:

$$\begin{bmatrix} x' \\ y' \\ z' \\ x \end{bmatrix} = \begin{bmatrix} 1 & 0 & 0 & -q_x^1 \\ 0 & 1 & 0 & -q_y^1 \\ 0 & 0 & 1 & -q_z^1 \\ 0 & 0 & 0 & 1 \end{bmatrix} \begin{bmatrix} x \\ y \\ z \\ x \end{bmatrix}, T_1 = \begin{bmatrix} 1 & 0 & 0 & -q_x^1 \\ 0 & 1 & 0 & -q_y^1 \\ 0 & 0 & 1 & -q_z^1 \\ 0 & 0 & 0 & 1 \end{bmatrix}.$$

At S203, a transformation matrix $T_2$ corresponding to the transformation from the plane $F_2'$ to a plane $F_2''$ is obtained, wherein the plane $F_2''$ is obtained by rotating the plane $F_2'$ around the origin of the coordinate system until its unit normal vector coincides with the unit normal vector of the plane $F_1$. The corresponding coordinate transformation is given by:

$$T_2 = \begin{bmatrix} 1 & 0 & 0 & 0 \\ 0 & \cos\theta_x^1 & \sin\theta_x^1 & 0 \\ 0 & -\sin\theta_x^1 & \cos\theta_x^1 & 0 \\ 0 & 0 & 0 & 1 \end{bmatrix} \begin{bmatrix} \cos\theta_y^1 & 0 & \sin\theta_y^1 & 0 \\ 0 & 1 & 0 & 0 \\ -\sin\theta_y^1 & 0 & \cos\theta_y^1 & 0 \\ 0 & 0 & 0 & 1 \end{bmatrix} \begin{bmatrix} \cos\theta_y^2 & 0 & -\sin\theta_y^2 & 0 \\ 0 & 1 & 0 & 0 \\ \sin\theta_y^2 & 0 & \cos\theta_y^2 & 0 \\ 0 & 0 & 0 & 1 \end{bmatrix}$$

$$\begin{bmatrix} 1 & 0 & 0 & 0 \\ 0 & \cos\theta_x^2 & -\sin\theta_x^2 & 0 \\ 0 & \sin\theta_x^2 & \cos\theta_x^2 & 0 \\ 0 & 0 & 0 & 1 \end{bmatrix}$$

$$\cos\theta_x^2 = \frac{n_z^2}{\sqrt{(n_y^2)^2 + (n_z^2)^2}}, \sin\theta_x^2 = \frac{n_y^2}{\sqrt{(n_y^2)^2 + (n_z^2)^2}},$$

$$\cos\theta_y^2 = \frac{\sqrt{(n_y^2)^2 + (n_z^2)^2}}{\sqrt{(n_x^2)^2 + (n_y^2)^2 + (n_z^2)^2}}, \sin\theta_y^2 = \frac{n_x^2}{\sqrt{(n_x^2)^2 + (n_y^2)^2 + (n_z^2)^2}},$$

$$\cos\theta_x^1 = \frac{n_z^1}{\sqrt{(n_y^1)^2 + (n_z^1)^2}}, \sin\theta_x^1 = \frac{n_y^1}{\sqrt{(n_y^1)^2 + (n_z^1)^2}},$$

$$\cos\theta_y^1 = \frac{\sqrt{(n_y^1)^2 + (n_z^1)^2}}{\sqrt{(n_x^1)^2 + (n_y^1)^2 + (n_z^1)^2}}, \sin\theta_y^1 = \frac{n_x^1}{\sqrt{(n_x^1)^2 + (n_y^1)^2 + (n_z^1)^2}},$$

The $F_2$ is translated until $Q_1$ coincides with the origin of the virtual coordinate system, thereby obtaining the plane $F_2'$. Then the unit normal vector of the plane $F_2'$ is rotated around the origin until it coincides with the unit normal vector $\vec{n}_1$ of the plane $F_1$; the angle at which the unit normal vector of the plane $F_2'$ has rotated counterclockwise around the x axis accordingly is $\theta_x^2$ or $2\pi-\theta_x^1$, and the angle at which the unit normal vector of the plane $F_2'$ has rotated counterclockwise around the y axis accordingly is $\theta_y^1$ or $2\pi-\theta_y^2$.

Through the above steps, the plane $F_2'$ can be rotated and transformed to obtain the plane $F_2''$.

At S204, a transformation matrix $T_3$ corresponding to the transformation from the plane $F_2''$ to a plane $F_2'''$ is obtained, wherein the plane $F_2'$ is obtained by translating the plane $F_2''$ until the sampling point coincident with the origin of the coordinate system in the first translation unit returns to its initial position. And the corresponding coordinate transformation is given by:

$$\begin{bmatrix} x' \\ y' \\ z' \\ x \end{bmatrix} = T_3 \begin{bmatrix} x \\ y \\ z \\ x \end{bmatrix}, T_3 = \begin{bmatrix} 1 & 0 & 0 & q_x^1 \\ 0 & 1 & 0 & q_y^1 \\ 0 & 0 & 1 & q_z^1 \\ 0 & 0 & 0 & 1 \end{bmatrix}.$$

At S205, the distance between the plane $F_2'''$ and the plane $F_1$ is obtained. Then a transformation matrix $T_4$ corresponding to the transformation from the plane $F_2'''$ to a plane $F_2''''$, wherein the plane $F_2''''$ is obtained by translating the plane $F_2'''$ along its unit normal vector by a vector $\vec{d}$ based on the distance to coincide with the plane $F_1$. And the corresponding coordinate transformation is given by:

$$\vec{d} = \left(-\overrightarrow{P_1 Q_1'} \cdot \vec{n_1}\right)\vec{n_1},$$

$$Q_1' = T_3 T_2 T_1 Q_1,$$

$$T_4 = \begin{bmatrix} 1 & 0 & 0 & d_x \\ 0 & 1 & 0 & d_y \\ 0 & 0 & 1 & d_z \\ 0 & 0 & 0 & 1 \end{bmatrix}.$$

In summary, the final transformation matrix is given by $T=T_4 T_3 T_2 T_1$.

For any point $(x, y, z)^T$ on the plane $F_2$, $(x', y', z', 1) = T(x, y, z, 1)^T$, wherein $(x', y', z')^T$ is the coordinate information after the transformation, and $(x, y, z)^T$ is the coordinate information before the transformation.

Thus points on the plane $F_1$ that correspond to the points on the plane $F_2$ can be found.

According to the above formulas, the points on the plane $F_1$ that correspond to the points $Q_1$, $Q_2$, and $Q_3$, which are on the plane $F_2$, can be found. So is the line that lies in the plane $F_2$ and bisects the Line Segment $Q_1$-$Q_2$. A path coincident with this line is the planned path L1 in the plane $F_1$.

At S300, according to the coordinate information of the second positioning devices 5, the coordinate information of the axis L2 of the virtual puncture needle and the apex C2 of the virtual puncture needle as projected onto the plane $F_1$ is obtained (i.e., transformed coordinate information) through planar matrix conversion, and the axis L2 of the virtual puncture needle and the apex C2 of the virtual puncture needle are represented in the coordinate system based on the transformed coordinate information.

Specifically, in the coordinate system, when the apex C1 of the fan-shaped ultrasound image of the lesion is taken as the origin, the transformation formula I is used for planar matrix conversion to obtain the corresponding axis L2 of the virtual puncture needle and apex C2 of the virtual puncture needle.

At S400, in the virtual coordinate system, the apex C2 of the virtual puncture needle and the apex C1 of the fan-shaped ultrasound image of the lesion are compared to see if they coincide, and the axis L2 of the virtual puncture needle and the planned path L1 are compared to see if they coincide. When the apex C2 of the virtual puncture needle and the apex C1 of the fan-shaped ultrasound image of the lesion coincide, and the axis L2 of the virtual puncture needle and the planned path L1 coincide, a judgment of coincidence is returned. The judgment of coincidence may be required before any puncture procedure.

More specifically, as shown in FIG. 8, first, a determination is made as to whether the apex C2 of the virtual puncture needle and the apex C1 of the fan-shaped ultrasound image of the lesion coincide; if not, then a judgment of "no coincidence" is returned; if yes, then another determination is made as to whether the axis L2 of the virtual puncture needle and the planed path L1 coincide. If the axis L2 of the virtual puncture needle and the planed path L1 coincide, then a judgment of coincidence is returned, and otherwise a judgment of "no coincidence" is returned. Corresponding signals indicating coincidence or the lack of it may be given. In one embodiment, the apex C2 of the virtual puncture needle serves as the axis to for the puncture needle to adjust its orientation, as shown in FIG. 7. Initially, the system's indicator light is red, and when the apex C2 of the virtual puncture needle and the apex C1 of the fan-shaped ultrasound image of the lesion coincide, the indicator light turns blue; when the axis L2 of the puncture needle coincides with the planned path L1, the indicator light turns green. The medical staff monitors information related to the coincidence or the lack of it of the axis L2 of the puncture needle and the planned path L1, and adjusts the puncture needle according to the color of the indicator light, which may be displayed on a virtual interface, during the movement of the puncture needle to assist the puncture procedure. The path suggested by a green indicator light is adopted to perform the puncturing.

Based on the transformation formula, a set of coordinate information can only correspond to one set of transformed coordinate information.

Similarly, there is only one line in the space whose transformed coordinate information corresponds to the axis of the fan-shaped ultrasound image of the lesion. Only when the axis of the puncture needle coincides with this line, can the corresponding axis of the virtual puncture needle coincide with the axis of the fan-shaped ultrasound image of the lesion (i.e., the planned path L1); when the axis of the puncture needle does not coincide with this line, the axis of the virtual puncture needle does not coincide with the planned path L1.

The present invention further provides a device, including: a memory and a processor. A computer program is stored in the memory, and the processor is configured to execute the computer program stored in the memory. When the computer program is executed, the puncture needle positioning method described in the present disclosure is realized.

The memory may include random access memory (RAM), and may also include non-volatile memory, for example, at least one disk memory.

The processor may be a general-purpose processor, including a central processing unit (CPU), a network processor (NP), etc.; it may also be a digital signal processor (DSP), Application Specific Integrated Circuit (ASIC), Field-Programmable Gate Array (Field-Programmable Gate Array, FPGA), other programming logic devices, discrete gates or transistor logic devices, or discrete hardware components.

The present disclosure also provides a computer-readable medium with computer programs stored thereon, that when executed by a processor, perform the puncture needle positioning method described herein.

The computer-readable medium, as a person of ordinary skill in the art can understand, perform all or part of the steps of the above-mentioned method's embodiments by computer program-related hardware. The aforementioned computer program can be stored in a computer-readable storage medium, which, when executed, performs the steps including the above-mentioned method's embodiments; and the computer-readable medium may be ROM, RAM, magnetic disks, optical disks, or other media that can store program codes.

Figure 9:
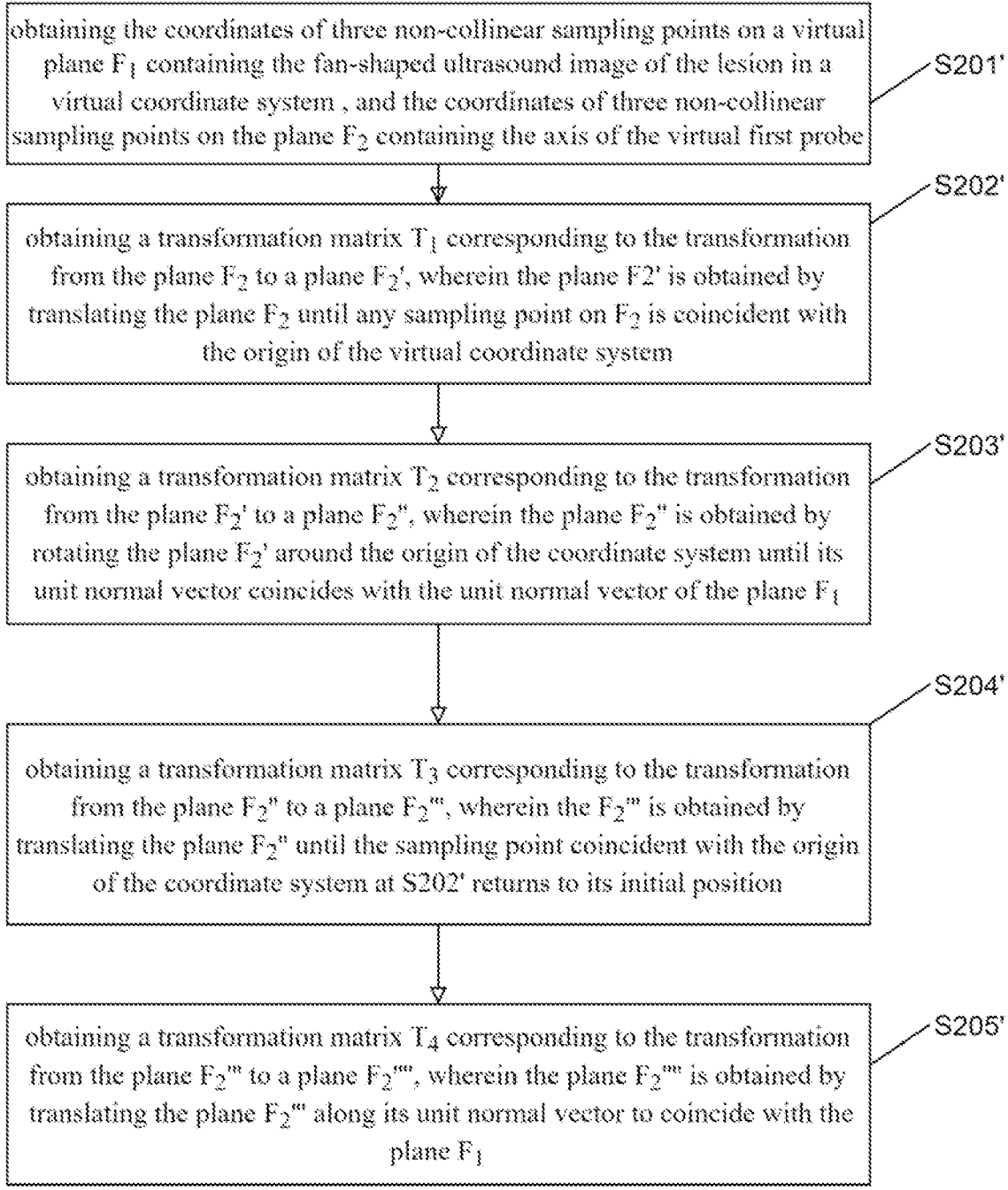
FIG. 9 is a flow chart illustrating a method for obtaining coordinates of a projection of an axis of an ultrasound probe on an ultrasound image according to some embodiments of the present disclosure

As shown in FIG. 9, the present disclosure also provides a method for positioning the axis of an ultrasound probe as projected onto a plane containing an ultrasound image, comprising:

S201' obtaining the coordinates of three non-collinear sampling points on a virtual plane $F_1$ containing the fan-shaped ultrasound image of the lesion in a virtual coordinate system $P_1(p_x^1,p_y^1,p_z^1)$, $P_2(p_x^2,p_y^2,p_z^2)$, $P_3(p_x^3,p_y^3,p_z^3)$, and the coordinates of three non-collinear sampling points on the plane $F_2$ containing the axis of a virtual ultrasound probe, $Q_1(q_x^1,q_y^1,q_z^1)$, $Q_2(q_x^2,q_y^2,q_z^2)$, $Q_3(q_x^3,q_y^3,q_z^3)$, wherein the virtual ultrasound probe is determined by first positioning devices on the ultrasound probe.

S202' obtaining a transformation matrix $T_1$ corresponding to the transformation from the plane $F_2$ to a plane $F_2'$, wherein the plane F2' is obtained by translating the plane $F_2$ until any sampling point on $F_2$ is coincident with the origin of the virtual coordinate system;

S203' obtaining a transformation matrix $T_2$ corresponding to the transformation from the plane $F_2'$ to a plane $F_2''$, wherein the plane $F_2''$ is obtained by rotating the plane $F_2'$ around the origin of the coordinate system until its unit normal vector coincides with the unit normal vector $\vec{n}_1$ of the plane $F_1$;

S204' obtaining a transformation matrix $T_3$ corresponding to the transformation from the plane $F_2''$ to a plane $F_2'''$, wherein the $F_2'''$ is obtained by translating the plane $F_2''$ until the sampling point coincident with the origin of the coordinate system in the first translation unit returns to its initial position;

S205' obtaining a transformation matrix $T_4$ corresponding to the transformation from the plane $F_2'''$ to a plane $F_2'''$, wherein the plane $F_2'''$ is obtained by first obtaining the distance between the plane $F_2'''$ and the plane $F_1$, and then translating the plane $F_2'''$ along its unit normal vector by a corresponding vector t to coincide with the plane $F_1$, wherein the coordinates of the projection of the axis of the ultrasound probe onto the plane $F_1$ can be obtained by using a coordinate transformation formula and the coordinates of the axis of the ultrasound probe on the plane $F_2$.

Specifically, at S201', the plane $F_1$ is a virtual plane displayed in the virtual coordinate system, which contains an ultrasound image of the lesion, obtained by scanning the lesion with the ultrasound probe 8. The plane $F_2$ is the plane containing the axis of the ultrasound probe 8 as shown in the virtual coordinates system when the ultrasound probe 8 is scanning the lesion to obtain the ultrasound image of the lesion. The plane $F_2$ can be located according to the sensors on the ultrasound probe 8.

In one embodiment, the virtual coordinate system also displays the apex of the fan-shaped ultrasound image of the lesion to assist in determining the puncture point. Specifically, the point where the ultrasound probe 8 is in contact with the patient's chest wall is represented in the virtual coordinate system as the apex of the fan-shaped ultrasound image of the lesion.

In one embodiment, the axis and plane containing the axis of the ultrasound probe 8 can be determined according to the positions of positioning devices 9 on the first probe 11. In one embodiment, in order to facilitate said determination, the positioning devices 9 are located on the axis of the ultrasound probe 8.

Figure 10:
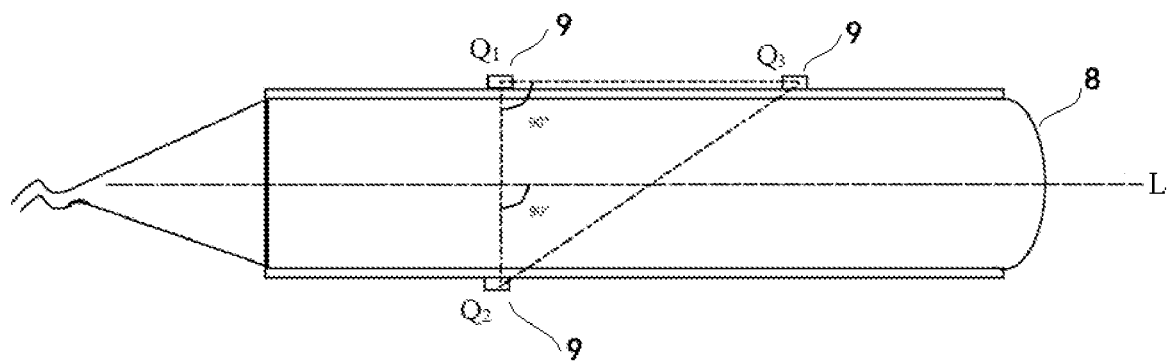
FIG. 10 is a schematic diagram of the structure of an ultrasound probe according to some embodiments of the present disclosure.

The positioning devices 9 may be sensors, and three non-collinear sensors $Q_1$, $Q_2$ and $Q_3$ as shown in FIG. 10 are provided on the axis of the ultrasound probe 8 to locate the axis L and plane containing the axis of the ultrasound probe 8.

The three non-collinear sensors $Q_1$, $Q_2$ and $Q_3$ constitute the vertices of a right triangle. This arrangement is for determining the axis of the ultrasound probe 8. The axis L of the ultrasound probe 8 lies in the plane containing Points $Q_1$, $Q_2$ and $Q_3$, and bisects Line Segment $Q_1$-$Q_2$.

In one embodiment, the virtual three-dimensional coordinate system uses the vertex of the fan-shaped ultrasound image of the lesion as the origin of the coordinate system. The plane containing the fan-shaped ultrasound image of the lesion is $F_1$.

In another embodiment, at S202', the plane $F_2$ is translated until Point $Q_1$ coincides with the origin of the coordinate system.

In one embodiment, the vertex of the fan-shaped ultrasound image of the lesion is taken as the origin of the coordinate system, and at S202' the plane $F_2$ of the virtual first probe is translated until $Q_1$ coincides with the origin, in which case, the coordinate transformation formula at S205' is given by:

$$(x',y',z',1) = T(x,y,z,1)^T,$$

wherein $(x', y', z')^T$ is the transformed coordinate information, and $(x, y, z)^T$ is the coordinate information before the transformation.

$$T = T_4 T_3 T_2 T_1,$$

wherein T is the transformation matrix corresponding to the projection of the axis of the virtual ultrasound probe onto the plane containing the fan-shaped ultrasound image of the lesion in the virtual coordinate system.

Specifically, at S202' the transformation matrix $T_1$ corresponding to the transformation from the plane $F_2$ to the plane $F_2'$ is given by:

$$T_1 = \begin{bmatrix} 1 & 0 & 0 & -q_x^1 \\ 0 & 1 & 0 & -q_y^1 \\ 0 & 0 & 1 & -q_z^1 \\ 0 & 0 & 0 & 1 \end{bmatrix}.$$

At S203', the transformation matrix $T_2$ corresponding to the transformation from the plane $F_2'$ to the plane $F_2''$ is given by:

$$T_2 = \begin{bmatrix} 1 & 0 & 0 & 0 \\ 0 & \cos\theta_x^1 & \sin\theta_x^1 & 0 \\ 0 & -\sin\theta_x^1 & \cos\theta_x^1 & 0 \\ 0 & 0 & 0 & 1 \end{bmatrix} \begin{bmatrix} \cos\theta_y^1 & 0 & \sin\theta_y^1 & 0 \\ 0 & 1 & 0 & 0 \\ -\sin\theta_y^1 & 0 & \cos\theta_y^1 & 0 \\ 0 & 0 & 0 & 1 \end{bmatrix} \begin{bmatrix} \cos\theta_y^2 & 0 & -\sin\theta_y^2 & 0 \\ 0 & 1 & 0 & 0 \\ \sin\theta_y^2 & 0 & \cos\theta_y^2 & 0 \\ 0 & 0 & 0 & 1 \end{bmatrix} \begin{bmatrix} 1 & 0 & 0 & 0 \\ 0 & \cos\theta_x^2 & -\sin\theta_x^2 & 0 \\ 0 & \sin\theta_x^2 & \cos\theta_x^2 & 0 \\ 0 & 0 & 0 & 1 \end{bmatrix}$$

At S204', the transformation matrix $T_3$ corresponding to the transformation from the plane $F_2''$ to the plane $F_2'''$ is given by:

$$T_3 = \begin{bmatrix} 1 & 0 & 0 & q_x^1 \\ 0 & 1 & 0 & q_y^1 \\ 0 & 0 & 1 & q_z^1 \\ 0 & 0 & 0 & 1 \end{bmatrix}.$$

At S205', the transformation matrix $T_4$ corresponding to the transformation from the plane $F_2'''$ to the plane $F_2''''$ is given by:

$$T_4 = \begin{bmatrix} 1 & 0 & 0 & d_x \\ 0 & 1 & 0 & d_y \\ 0 & 0 & 1 & d_z \\ 0 & 0 & 0 & 1 \end{bmatrix}$$

wherein $$\cos\theta_x^2 = \frac{n_z^2}{\sqrt{(n_y^2)^2 + (n_z^2)^2}}, \sin\theta_x^2 = \frac{n_y^2}{\sqrt{(n_y^2)^2 + (n_z^2)^2}},$$

$$\cos\theta_y^2 = \frac{\sqrt{(n_y^2)^2 + (n_z^2)^2}}{\sqrt{(n_x^2)^2 + (n_y^2)^2 + (n_z^2)^2}}, \sin\theta_y^2 = \frac{n_x^2}{\sqrt{(n_x^2)^2 + (n_y^2)^2 + (n_z^2)^2}},$$

$$\cos\theta_x^1 = \frac{n_z^1}{\sqrt{(n_y^1)^2 + (n_z^1)^2}}, \sin\theta_x^1 = \frac{n_y^1}{\sqrt{(n_y^1)^2 + (n_z^1)^2}},$$

$$\cos\theta_y^1 = \frac{\sqrt{(n_y^1)^2 + (n_z^1)^2}}{\sqrt{(n_x^1)^2 + (n_y^1)^2 + (n_z^1)^2}}, \sin\theta_y^1 = \frac{n_x^1}{\sqrt{(n_x^1)^2 + (n_y^1)^2 + (n_z^1)^2}}.$$

$\vec{n}_1$ is a unit normal vector of the plane $F_1$, and i is a unit normal vector of the plane $F_2$.

$$\vec{n}_1 = \frac{\overrightarrow{P_1P_2} \times \overrightarrow{P_1P_3}}{|\overrightarrow{P_1P_2}||\overrightarrow{P_1P_3}|}, \vec{n}_2 = \frac{\overrightarrow{Q_1Q_2} \times \overrightarrow{Q_1Q_3}}{|\overrightarrow{Q_1Q_2}||\overrightarrow{Q_1Q_3}|},$$

$$\vec{n}_1 = (n_x^1, n_y^1, n_z^1), = \vec{n}_2 = (n_x^2, n_y^2, n_z^2).$$

The plane $F_2'''$ is translated by the vector 7 to obtain the plane $F_2''''$, and is given by:

$$\vec{d} = (-\overrightarrow{P_1Q_1'} \cdot \vec{n}_1)\vec{n}_1, \vec{d} = (d_x, d_y, d_z), Q_1' = T_3 T_2 T_1 Q_1.$$

The explanation of the above formulas is as follows:

At S202', the plane $F_2'$ is obtained by translating the plane $F_2$ until any sampling point on the plane $F_2$ is coincident with the origin of the virtual coordinate system. In one embodiment, the plane $F_2$ is translated until Point $Q_1$ coincides with the origin of the virtual coordinate system, and the corresponding transformation matrix $T_1$ is given by:

$$T_1 = \begin{bmatrix} 1 & 0 & 0 & -q_x^1 \\ 0 & 1 & 0 & -q_y^1 \\ 0 & 0 & 1 & -q_z^1 \\ 0 & 0 & 0 & 1 \end{bmatrix}.$$

The coordinates of points on the plane $F_2'$ are given by:

$$\begin{bmatrix} x' \\ y' \\ z' \\ 1 \end{bmatrix} = \begin{bmatrix} 1 & 0 & 0 & -q_x^1 \\ 0 & 1 & 0 & -q_y^1 \\ 0 & 0 & 1 & -q_z^1 \\ 0 & 0 & 0 & 1 \end{bmatrix} \begin{bmatrix} x \\ y \\ z \\ 1 \end{bmatrix}$$

At S203', the plane $F_2''$ is obtained by rotating the plane $F_2'$ around the origin of the coordinate system until its unit normal vector coincides with the unit normal vector of the plane $F_1$; the corresponding transformation matrix $T_2$ is given by:

$$T_2 = \begin{bmatrix} 1 & 0 & 0 & 0 \\ 0 & \cos\theta_x^1 & \sin\theta_x^1 & 0 \\ 0 & -\sin\theta_x^1 & \cos\theta_x^1 & 0 \\ 0 & 0 & 0 & 1 \end{bmatrix} \begin{bmatrix} \cos\theta_y^1 & 0 & \sin\theta_y^1 & 0 \\ 0 & 1 & 0 & 0 \\ -\sin\theta_y^1 & 0 & \cos\theta_y^1 & 0 \\ 0 & 0 & 0 & 1 \end{bmatrix} \begin{bmatrix} \cos\theta_y^2 & 0 & -\sin\theta_y^2 & 0 \\ 0 & 1 & 0 & 0 \\ \sin\theta_y^2 & 0 & \cos\theta_y^2 & 0 \\ 0 & 0 & 0 & 1 \end{bmatrix}$$

$$\begin{bmatrix} 1 & 0 & 0 & 0 \\ 0 & \cos\theta_x^2 & -\sin\theta_x^2 & 0 \\ 0 & \sin\theta_x^2 & \cos\theta_x^2 & 0 \\ 0 & 0 & 0 & 1 \end{bmatrix}$$

wherein $$\cos\theta_x^2 = \frac{n_z^2}{\sqrt{(n_y^2)^2 + (n_z^2)^2}}, \quad \sin\theta_x^2 = \frac{n_y^2}{\sqrt{(n_y^2)^2 + (n_z^2)^2}},$$

$$\cos\theta_y^2 = \frac{\sqrt{(n_y^2)^2 + (n_z^2)^2}}{\sqrt{(n_x^2)^2 + (n_y^2)^2 + (n_z^2)^2}}, \quad \sin\theta_y^2 = \frac{n_x^2}{\sqrt{(n_x^2)^2 + (n_y^2)^2 + (n_z^2)^2}},$$

$$\cos\theta_x^1 = \frac{n_z^1}{\sqrt{(n_y^1)^2 + (n_z^1)^2}}, \quad \sin\theta_x^1 = \frac{n_y^1}{\sqrt{(n_y^1)^2 + (n_z^1)^2}},$$

$$\cos\theta_y^1 = \frac{\sqrt{(n_y^1)^2 + (n_z^1)^2}}{\sqrt{(n_x^1)^2 + (n_y^1)^2 + (n_z^1)^2}}, \quad \sin\theta_y^1 = \frac{n_x^1}{\sqrt{(n_x^1)^2 + (n_y^1)^2 + (n_z^1)^2}}.$$

The plane $F_2$ is translated until $Q_1$ coincides with the origin of the virtual coordinate system, thereby obtaining the plane $F_2'$. Then the unit normal vector of the plane $F_2'$ is rotated around the origin until it coincides with the unit normal vector $\vec{n}_1$ of the plane $F_1$; the angle at which the unit normal vector of the plane $F_2'$ has rotated counterclockwise around the x axis accordingly is $\theta_x^2$ or $2\pi - \theta_x^1$, and the angle at which the unit normal vector of the plane $F_2'$ has rotated counterclockwise around the y axis accordingly is $\theta_y^1$ or $2\pi - \theta_y^2$.

Through the above process, the plane $F_2'$ can be rotated and transformed to obtain the plane $F_2''$.

At S204', the plane $F_2'''$ is obtained by translating the plane $F_2''$ until the sampling point coincident with the origin of the coordinate system at S202' returns to its initial position. When the sample point is $Q_1$, the corresponding transformation is given by:

$$\begin{bmatrix} x' \\ y' \\ z' \\ 1 \end{bmatrix} = T_3 \begin{bmatrix} x \\ y \\ z \\ 1 \end{bmatrix}, \text{ wherein, } T_3 = \begin{bmatrix} 1 & 0 & 0 & q_x^1 \\ 0 & 1 & 0 & q_y^1 \\ 0 & 0 & 1 & q_z^1 \\ 0 & 0 & 0 & 1 \end{bmatrix}.$$

At S205', the distance between the plane $F_2'''$ and the plane $F_1$ is first obtained, then the plane $F_2'''$ is translated along its unit normal vector by the corresponding vector el to coincide with the plane $F_1$, thereby obtaining the plane $F_2''''$. The vector is given by:

$$\vec{d} = (-\vec{P_1Q'_1} \cdot \vec{n}_1)\vec{n}_1, \text{ wherein } Q'_1 = T_3 T_2 T_1 Q_1.$$

The corresponding transformation matrix T4 is given by:

$$T_4 = \begin{bmatrix} 1 & 0 & 0 & d_x \\ 0 & 1 & 0 & d_y \\ 0 & 0 & 1 & d_z \\ 0 & 0 & 0 & 1 \end{bmatrix}.$$

In summary, the final transformation matrix is given by $T = T_4 T_3 T_2 T_1$.

For any point $(x, y, z)^T$ on the plane $F_2$, $(x', y', z', 1) = T(x, y, z, 1)^T$, wherein $(x', y', z')^T$ is the coordinate information after the transformation, and $(x, y, z)^T$ is the coordinate information before the transformation. Thus points on the plane $F_1$ that correspond to the points on the plane $F_2$ of the virtual first probe can be found.

According to the above formulas, the points on the plane $F_1$ that correspond to the points $Q_1$, $Q_2$, and $Q_3$, which are on the plane $F_2$, can be found. So is the line that lies in the plane $F_2$ and bisects the Line Segment $Q_1$-$Q_2$. A path coincident with this line is the planned path L1 in the plane $F_1$.

Therefore, according to the coordinate information of the ultrasound probe 8 in the virtual coordinate system, the position of the axis of the virtual ultrasound probe 8 on the plane $F_1$ can be obtained by the method of the present disclosure, which can be used as a planned path for transthoracic puncture.

More on determining the planned path by the axis obtained by the method of the present disclosure:

The ultrasound image of the lesion is fan-shaped. Under normal circumstances, a line segment passing through the apex of the fan-shaped ultrasound image of the lesion and the puncture sampling point can be used as the planned path. When the puncture sampling point is placed on the axis ultrasound image of the lesion, the axis of the ultrasound image of the lesion can be used as the planned path. In real situations, the axis L of the ultrasound probe 8 should be located on the plane containing the ultrasound image of the lesion, and the apex of the ultrasound probe coincides with the apex of the ultrasound image of the lesion, and the axis L of the ultrasound probe 8 coincides with the axis of the fan-shaped ultrasound image of the lesion. Therefore, the planned path can be determined by determining the position of the ultrasound probe's axis. But in the virtual coordinate system, the relative positions of the ultrasound image of the lesion and the axis L of the ultrasound probe 8 do not match the actual relative positions of the two. Therefore, the coordinate transformation formulas described in the method of the present disclosure may be used for conversion, to project the axis L of the ultrasound probe 8 onto the ultrasound image of the lesion.

The present disclosure also provides a device for locating the axis of the ultrasound probe as projected onto the plane containing the ultrasound image, including a sampling unit, used to obtain the coordinates of three non-collinear sampling points on the plane $F_1$ containing the ultrasound image of the lesion in a virtual coordinate system $P_1(p_x^1, p_y^1, p_z^1)$, $P_2(p_x^2, p_y^2, p_z^2)$, $P_3(p_x^3, p_y^3, p_z^3)$, and the coordinates of three non-collinear sampling points on the plane $F_2$ $Q_1(q_x^1, q_y^1, q_z^1)$, $Q_2(q_x^2, q_y^2, q_z^2)$, $Q_3(q_x^3, q_y^3, q_z^3)$;

a first translation unit, used to obtain the transformation matrix $T_1$ corresponding to the transformation from the plane $F_2$ to the plane $F_2'$, wherein the plane $F_2'$ is obtained by translating the plane $F_2$ until any sampling point on $F_2$ is coincident with the origin of the virtual coordinate system;

a rotation unit, used to obtain the transformation matrix $T_2$ corresponding to the transformation from the plane $F_2'$ to the plane $F_2''$, wherein the plane $F_2''$ is obtained by rotating the plane $F_2'$ around the origin of the coordinate system until its unit normal vector coincides with the unit normal vector of the plane $F_1$;

a second translation unit, used to obtain the transformation matrix $T_3$ corresponding to the transformation from the plane $F_2''$ to the plane $F_2'''$, wherein the $F_2'''$ is obtained by translating the plane $F_2''$ until the sampling point coincident with the origin of the coordinate system in the first translation unit returns to its initial position;

a third translation unit, used to obtain the transformation matrix $T_4$ corresponding to the transformation from the plane $F_2'''$ to a plane $F_2''''$, wherein the plane $F_2''''$ is obtained by first obtaining the distance between the plane $F_2'''$ and the plane $F_1$, and then translating the plane $F_2'''$ along its unit normal vector by the vector $\vec{d}$ to coincide with the plane $F_1$, wherein the coordinates of the projection of the axis of the virtual ultrasound probe onto the plane $F_1$ can be obtained by using a coordinate transformation formula and the coordinates of the axis of the virtual ultrasound probe on the plane $F_2$.

Specifically, in the sampling unit, the plane $F_1$ is a virtual plane displayed in the virtual coordinate system, which contains an ultrasound image of the lesion, obtained by scanning the lesion with the ultrasound probe 8. The plane $F_2$ is a plane containing the axis of the ultrasound probe 8 as shown in the virtual coordinates system when the ultrasound probe 8 is scanning the lesion to obtain the ultrasound image of the lesion. The plane $F_2$ can be located according to the sensors on the ultrasound probe 8.

In one embodiment, the virtual coordinate system also displays the apex of the fan-shaped ultrasound image of the lesion to assist in determining the puncture point. Specifically, the point where the ultrasound probe 8 is in contact with the patient's chest wall is represented in the virtual coordinate system as the apex of the fan-shaped ultrasound image of the lesion.

In one embodiment, the axis and plane containing the axis of the ultrasound probe 8 can be determined according to the positions of the positioning devices 9 on the ultrasound probe 8. In one embodiment, in order to facilitate said determination, the positioning devices 9 are located on the axis of the ultrasound probe 8.

The positioning devices 9 may be sensors, and the three non-collinear sensors $Q_1$, $Q_2$ and $Q_3$ as shown in FIG. 2 are provided on the axis of the ultrasound probe 8 to locate the axis and plane containing the axis of the ultrasound probe 8.

The three non-collinear sensors $Q_1$, $Q_2$ and $Q_3$ constitute the vertices of a right triangle. This arrangement is for determining the axis of the ultrasound probe 8 by the positioning devices 9. The axis of the ultrasound probe 8 lies in the plane containing Points $Q_1$, $Q_2$ and $Q_3$, and bisects Line Segment $Q_1$-$Q_2$.

In one embodiment, the virtual three-dimensional coordinate system uses the vertex of the fan-shaped ultrasound image of the lesion as the origin of the coordinate system. The plane containing the fan-shaped ultrasound image of the lesion is the plane $F_1$.

In another embodiment, in the first translation unit, the plane $F_2$ is translated until Point $Q_1$ coincides with the origin of the coordinate system.

The vertex of the fan-shaped ultrasound image of the lesion is taken as the origin of the coordinate system, and the plane $F_2$ is translated until $Q_1$ coincides with the origin, thereby obtaining the plane $F_2'$. And the corresponding transformation is given by:

$$\begin{bmatrix} x' \\ y' \\ z' \\ 1 \end{bmatrix} = \begin{bmatrix} 1 & 0 & 0 & -q_x^1 \\ 0 & 1 & 0 & -q_y^1 \\ 0 & 0 & 1 & -q_z^1 \\ 0 & 0 & 0 & 1 \end{bmatrix} \begin{bmatrix} x \\ y \\ z \\ 1 \end{bmatrix},$$

wherein the transformation matrix $T_1$ corresponding to the transformation from the plane $F_2$ to the plane $F_2'$ is given by:

$$T_1 = \begin{bmatrix} 1 & 0 & 0 & -q_x^1 \\ 0 & 1 & 0 & -q_y^1 \\ 0 & 0 & 1 & -q_z^1 \\ 0 & 0 & 0 & 1 \end{bmatrix}.$$

In the rotation unit, the transformation matrix $T_2$ corresponding to the transformation from the plane $F_2'$ to the plane $F_2''$ is given by:

$$T_2 = \begin{bmatrix} 1 & 0 & 0 & 0 \\ 0 & \cos\theta_x^1 & \sin\theta_x^1 & 0 \\ 0 & -\sin\theta_x^1 & \cos\theta_x^1 & 0 \\ 0 & 0 & 0 & 1 \end{bmatrix} \begin{bmatrix} \cos\theta_y^1 & 0 & \sin\theta_y^1 & 0 \\ 0 & 1 & 0 & 0 \\ -\sin\theta_y^1 & 0 & \cos\theta_y^1 & 0 \\ 0 & 0 & 0 & 1 \end{bmatrix} \begin{bmatrix} \cos\theta_y^2 & 0 & -\sin\theta_y^2 & 0 \\ 0 & 1 & 0 & 0 \\ \sin\theta_y^2 & 0 & \cos\theta_y^2 & 0 \\ 0 & 0 & 0 & 1 \end{bmatrix}$$

$$\begin{bmatrix} 1 & 0 & 0 & 0 \\ 0 & \cos\theta_x^2 & -\sin\theta_x^2 & 0 \\ 0 & \sin\theta_x^2 & \cos\theta_x^2 & 0 \\ 0 & 0 & 0 & 1 \end{bmatrix}$$

In the second translation unit, the transformation matrix $T_3$ corresponding to the transformation from the plane $F_2''$ to the plane $F_2'''$ is given by:

$$T_3 = \begin{bmatrix} 1 & 0 & 0 & q_x^1 \\ 0 & 1 & 0 & q_y^1 \\ 0 & 0 & 1 & q_z^1 \\ 0 & 0 & 0 & 1 \end{bmatrix}.$$

In the third translation unit, the transformation matrix $T_4$ corresponding to the transformation from the plane $F_2'''$ to the plane $F_2''''$ is given by:

$$T_4 = \begin{bmatrix} 1 & 0 & 0 & d_x \\ 0 & 1 & 0 & d_y \\ 0 & 0 & 1 & d_z \\ 0 & 0 & 0 & 1 \end{bmatrix}.$$

$$\cos\theta_x^2 = \frac{n_z^2}{\sqrt{(n_y^2)^2 + (n_z^2)^2}}, \sin\theta_x^2 = \frac{n_y^2}{\sqrt{(n_y^2)^2 + (n_z^2)^2}},$$

$$\cos\theta_y^2 = \frac{\sqrt{(n_y^2)^2 + (n_z^2)^2}}{\sqrt{(n_x^2)^2 + (n_y^2)^2 + (n_z^2)^2}}, \sin\theta_y^2 = \frac{n_x^2}{\sqrt{(n_x^2)^2 + (n_y^2)^2 + (n_z^2)^2}},$$

$$\cos\theta_x^1 = \frac{n_z^1}{\sqrt{(n_y^1) + (n_z^1)^2}}, \sin\theta_x^1 = \frac{n_y^1}{\sqrt{(n_y^1)^2 + (n_z^1)^2}},$$

$$\cos\theta_y^1 = \frac{\sqrt{(n_y^1)^2 + (n_z^1)^2}}{\sqrt{(n_x^1)^2 + (n_y^1)^2 + (n_z^1)^2}}, \sin\theta_y^1 = \frac{n_x^1}{\sqrt{(n_x^1)^2 + (n_y^1)^2 + (n_z^1)^2}}.$$

$\vec{n}_1$ is a unit normal vector of the plane $F_1$, and $\vec{n}_2$ is a unit normal vector of the plane $F_2$.

$$\vec{n}_1 = \frac{\overrightarrow{P_1P_2} \times \overrightarrow{P_1P_3}}{|\overrightarrow{P_1P_2}||\overrightarrow{P_1P_3}|}, \vec{n}_2 = \frac{\overrightarrow{Q_1Q_2} \times \overrightarrow{Q_1Q_3}}{|\overrightarrow{Q_1Q_2}||\overrightarrow{Q_1Q_3}|},$$

$$\vec{n}_1 = (n_x^1, n_y^1, n_z^1), \vec{n}_2 = (n_x^2, n_y^2, n_z^2).$$

The plane $F_2'''$ is translated by the vector $\vec{d}$ to obtain the plane $F_2''''$, and $\vec{d}$ is given by:

$$\vec{d} = (-\overrightarrow{P_1Q_1} \cdot \vec{n}_1)\vec{n}_1, \vec{d} = (d_x, d_y, d_z), Q'_1 = T_3T_2T_1Q_1.$$

The explanation of the above formulas is as follows:

In the first translation unit, the plane $F_2'$ is obtained by translating the plane $F_2$ until any sampling point on $F_2$ is coincident with the origin of the virtual coordinate system. In one embodiment, the plane $F_2$ is translated until Point $Q_1$ coincides with the origin of the virtual coordinate system, and the corresponding transformation matrix $T_1$ is given by:

$$T_1 = \begin{bmatrix} 1 & 0 & 0 & -q_x^1 \\ 0 & 1 & 0 & -q_y^1 \\ 0 & 0 & 1 & -q_z^1 \\ 0 & 0 & 0 & 1 \end{bmatrix}.$$

The coordinates of points on the plane $F_2'$ are given by:

$$\begin{bmatrix} x' \\ y' \\ z' \\ 1 \end{bmatrix} = \begin{bmatrix} 1 & 0 & 0 & -q_x^1 \\ 0 & 1 & 0 & -q_y^1 \\ 0 & 0 & 1 & -q_z^1 \\ 0 & 0 & 0 & 1 \end{bmatrix} \begin{bmatrix} x \\ y \\ z \\ 1 \end{bmatrix}.$$

In the rotation unit, the plane $F_2''$ is obtained by rotating the plane $F_2'$ around the origin of the coordinate system until its unit normal vector coincides with the unit normal vector of the plane $F_1$; the corresponding transformation matrix $T_2$ is given by:

$$T_2 = \begin{bmatrix} 1 & 0 & 0 & 0 \\ 0 & \cos\theta_x^1 & \sin\theta_x^1 & 0 \\ 0 & -\sin\theta_x^1 & \cos\theta_x^1 & 0 \\ 0 & 0 & 0 & 1 \end{bmatrix} \begin{bmatrix} \cos\theta_y^1 & 0 & \sin\theta_y^1 & 0 \\ 0 & 1 & 0 & 0 \\ -\sin\theta_y^1 & 0 & \cos\theta_y^1 & 0 \\ 0 & 0 & 0 & 1 \end{bmatrix} \begin{bmatrix} \cos\theta_y^2 & 0 & -\sin\theta_y^2 & 0 \\ 0 & 1 & 0 & 0 \\ \sin\theta_y^2 & 0 & \cos\theta_y^2 & 0 \\ 0 & 0 & 0 & 1 \end{bmatrix}$$

$$\begin{bmatrix} 1 & 0 & 0 & 0 \\ 0 & \cos\theta_x^2 & -\sin\theta_x^2 & 0 \\ 0 & \sin\theta_x^2 & \cos\theta_x^2 & 0 \\ 0 & 0 & 0 & 1 \end{bmatrix}$$

$$\cos\theta_x^2 = \frac{n_z^2}{\sqrt{(n_y^2)^2 + (n_z^2)^2}}, \sin\theta_x^2 = \frac{n_y^2}{\sqrt{(n_y^2)^2 + (n_z^2)^2}},$$

$$\cos\theta_y^2 = \frac{\sqrt{(n_y^2)^2 + (n_z^2)^2}}{\sqrt{(n_x^2)^2 + (n_y^2)^2 + (n_z^2)^2}}, \sin\theta_y^2 = \frac{n_x^2}{\sqrt{(n_x^2)^2 + (n_y^2)^2 + (n_z^2)^2}},$$

$$\cos\theta_x^1 = \frac{n_z^1}{\sqrt{(n_y^1) + (n_z^1)^2}}, \sin\theta_x^1 = \frac{n_y^1}{\sqrt{(n_y^1)^2 + (n_z^1)^2}},$$

$$\cos\theta_y^1 = \frac{\sqrt{(n_y^1)^2 + (n_z^1)^2}}{\sqrt{(n_x^1)^2 + (n_y^1)^2 + (n_z^1)^2}}, \sin\theta_y^1 = \frac{n_x^1}{\sqrt{(n_x^1)^2 + (n_y^1)^2 + (n_z^1)^2}}.$$

The plane $F_2$ is translated until $Q_1$ coincides with the origin of the virtual coordinate system, thereby obtaining the plane $F_2'$. Then the unit normal vector of the plane $F_2'$ is rotated around the origin until it coincides with the unit normal vector $\vec{n}_1$ of the plane $F_1$; the angle at which the unit normal vector of the plane $F_2'$ has rotated counterclockwise around the x axis accordingly is $\theta_x^2$ or $2\pi - \theta_x^1$, and the angle at which the unit normal vector of the plane $F_2'$ has rotated counterclockwise around the y axis accordingly is $\theta_y^1$ or $2\pi - \theta_y^2$.

Through the above process, the plane $F_2'$ can be rotated and transformed to obtain the plane $F_2''$.

In the second translation unit, the plane $F_2'''$ is obtained by translating the plane $F_2''$ until the sampling point coincident with the origin of the coordinate system at S202' returns to its initial position. When the sample point is $Q_1$, the corresponding transformation is given by:

$$\begin{bmatrix} x' \\ y' \\ z' \\ 1 \end{bmatrix} = T_3 \begin{bmatrix} x \\ y \\ z \\ 1 \end{bmatrix},$$

wherein $$T_3 = \begin{bmatrix} 1 & 0 & 0 & q_x^1 \\ 0 & 1 & 0 & q_y^1 \\ 0 & 0 & 1 & q_z^1 \\ 0 & 0 & 0 & 1 \end{bmatrix}.$$

In the third translation unit, the distance between the plane $F_2'''$ and the plane $F_1$ is first obtained, then the plane $F_2'''$ is translated along its unit normal vector by the corresponding vector $\vec{d}$ to coincide with the plane $F_1$, thereby obtaining the plane $F_2$. The vector is given by:

$$\vec{d} = (-\overrightarrow{P_1Q_1'} \cdot \vec{n_1})\vec{n_1},$$

wherein $$Q_1' = T_2 T_2 T_1 Q_1.$$

The corresponding transformation matrix T4 is given by:

$$T_4 = \begin{bmatrix} 1 & 0 & 0 & d_x \\ 0 & 1 & 0 & d_y \\ 0 & 0 & 1 & d_z \\ 0 & 0 & 0 & 1 \end{bmatrix}.$$

In summary, the final transformation matrix is given by $T = T_4 T_3 T_2 T_1$.

For any point $(x, y, z)^T$ on the plane $F_2$, $(x', y', z', 1) = T(x, y, z, 1)^T$, wherein $(x', y', z')^T$ is the coordinate information after the transformation, and $(x, y, z)^T$ is the coordinate information before the transformation. Thus points on the plane $F_1$ that correspond to the points on the plane $F_2$ of the virtual first probe can be found.

According to the above formulas, the points on the plane $F_1$ that correspond to the points $Q_1$, $Q_2$, and $Q_3$, which are on the plane $F_2$, can be found. So is the line that lies in the plane $F_2$ and bisects the Line Segment $Q_1$-$Q_2$. A path coincident with this line is the planned path L1 in the plane $F_1$.

Therefore, according to the coordinate information of the ultrasound probe 8 in the virtual coordinate system, the position of the axis of the virtual ultrasound probe 8 on the plane $F_1$ can be obtained by the method of the present disclosure, which can be used as a planned path for transthoracic puncture.

More on determining the planned path by the axis of the ultrasound probe obtained by the method of the present disclosure:

The ultrasound image of the lesion is fan-shaped. Under normal circumstances, a line segment passing through the apex of the fan-shaped ultrasound image of the lesion and the puncture sampling point can be used as the planned path. When the puncture sampling point is placed on the axis ultrasound image of the lesion, the axis of the ultrasound image of the lesion can be used as the planned path. In real situations, the axis L of the ultrasound probe 8 should be located on the plane containing the ultrasound image of the lesion, and the apex of the ultrasound probe coincides with the apex of the ultrasound image of the lesion, and the axis L of the ultrasound probe 8 coincides with the axis of the fan-shaped ultrasound image of the lesion. Therefore, the planned path can be determined by determining the position of the ultrasound probe's axis. But in the virtual coordinate system, the relative positions of the ultrasound image of the lesion and the axis L of the ultrasound probe 8 do not match the actual relative positions of the two. Therefore, the coordinate transformation formulas described in the method of the present disclosure may be used for conversion, to project the axis L of the ultrasound probe 8 onto the ultrasound image of the lesion.

The present disclosure also provides a computer-readable medium with computer programs stored thereon, that when executed by a processor, perform the method for positioning the axis of an ultrasound probe as projected onto the plane containing the ultrasound image as described herein.

The computer-readable medium, as a person of ordinary skill in the art can understand, perform all or part of the steps of the above-mentioned method's embodiments by computer program-related hardware. The aforementioned computer program can be stored in a computer-readable storage medium, which, when executed, performs the steps including the above-mentioned method's embodiments; and the computer-readable medium may be ROM, RAM, magnetic disks, optical disks, or other media that can store program codes.

The present invention further provides a device, including: a memory and a processor. A computer program is stored in the memory, and the processor is configured to execute the computer program stored in the memory. When the computer program is executed, the method for positioning the axis of an ultrasound probe as projected onto the plane containing the ultrasound image as described herein is realized.

The memory may include random access memory (RAM), and may also include non-volatile memory, for example, at least one disk memory.

The processor may be a general-purpose processor, including a central processing unit (CPU), a network processor (NP), etc.; it may also be a digital signal processor (DSP), Application Specific Integrated Circuit (ASIC), Field-Programmable Gate Array (Field-Programmable Gate Array, FPGA), other programming logic devices, discrete gates or transistor logic devices, or discrete hardware components.

In summary, the puncture needle positioning system and method provided by the present disclosure can greatly improve the accuracy of transthoracic puncture. Not only can the invention effectively avoid the complications caused by repeated puncture, but also greatly shorten the puncture time during surgery. Adopting the first positioning device and the second positioning device greatly improves the conventional single ultrasound positioning and navigation technique, and can digitally analyze all position information. Various kinds of position information in the magnetic field can be obtained through the first positioning devices and the second positioning devices, and transformed into three-dimensional information displayed in a three-dimensional coordinate system. The system provides accurate puncture path planning tailored for different individuals, and realizes individualized and precise medical treatment for patients, which will greatly reduce surgery-related complications and make it possible for transthoracic puncture interventional treatment to become a conventional treatment method. The method of obtaining the axis of the virtual ultrasound probe as projected onto the ultrasound image provided is by the present disclosure can display the ultrasound image of the lesion and the plane where the positioning devices of the virtual ultrasound probe are located in the same virtual coordinate system, in order to obtain the planned path. The present disclosure provides a standardized technical scheme for transthoracic puncture intracardiac interventional therapy. Through the implementation of the scheme of the present disclosure, the preoperative planned puncture path can be accurately recorded and visualized, to provide a reliable guidance for the medical staff during operation, and effectively reduces the medical staff's error rate in terms of selecting the puncture point. The present disclosure can not only improve the puncture success rate, but also effectively prevent the occurrence of complications and improve the safety of the operation.

While particular elements, embodiments, and applications of the present invention have been shown and described, it is understood that the invention is not limited thereto because modifications may be made by those skilled in the art, particularly in light of the foregoing teaching. It is therefore contemplated by the appended claims to cover such modifications and incorporate those features which come within the spirit and scope of the invention.

What is claimed is:

1. A puncture needle positioning system, comprising:
an ultrasound unit (1), including a first probe (11) for providing an ultrasound image of a lesion, wherein a plurality of first positioning devices (4) for providing coordinate information of the first probe (11) are provided on the first probe (11);
a puncture needle unit (2), including a puncture needle, wherein a plurality of second positioning devices (5) for providing coordinate information of the puncture needle are provided on the puncture needle; and
a processing and display unit (3), communicatively connected with the ultrasound unit (1), each of the first positioning devices (4), and each of the second positioning devices (5) respectively;
wherein the ultrasound image of the lesion provided by the first probe (11) is displayed in a virtual coordinate system by the processing and display unit (3);
wherein the coordinate information of the first probe (11) when the first probe (11) is acquiring the ultrasound image of the lesion is sent to the processing and display unit (3);
wherein the processing and display unit (3) determines a planned path (L1) in the virtual coordinate system;
wherein the processing and display unit (3) obtains the coordinate information of the puncture needle provided by each of the second positioning device (5), and displays an axis (L2) of a virtual puncture needle that corresponds to the puncture needle, and a vertex (C2) of the virtual puncture needle in the virtual coordinate system;
wherein the processing and display unit (3), in the virtual coordinate system, compares the axis (L2) of the virtual puncture needle with the planned path (L1) to see if they are coincident;
wherein the processing and display unit (3) further includes a processor; a display; and a plurality of memory units;
wherein the plurality of memory units includes a first memory unit for storing the ultrasound image of the lesion, a second memory unit for storing the coordinate information of the first probe (11), a third memory unit for converting coordinate information of the ultrasound image to an axis of the first probe (11), a fourth memory unit for storing the coordinate information provided by the second positioning devices (5);
wherein the processor is electrically connected to the display and the memory units, and is in data communication with the first probe, the first positioning devices, and the second positioning devices;
wherein the processor receives data representing the ultrasound image of the lesion from the first probe, and data representing the coordinate information of the first probe from the first positioning devices when the first probe is acquiring the ultrasound image of the lesion, and stores the data representing the ultrasound image and the data representing the coordinate information in corresponding memory units, and sends the data representing the ultrasound image and the data representing the coordinate information to the display;
wherein the display receives the data representing the ultrasound image and the data representing the coordinate information from the processor the processor and transforms the data representing the ultrasound image and the data representing the coordinate information into light signals representing the ultrasound image of the lesion and the first probe in the virtual coordinate system;
wherein the processor determines the planned path (L1) in the virtual coordinate system;
wherein the processor receives data representing the coordinate information of the second positioning devices from the second positioning devices and stores the data representing the coordinate information of the second positioning devices in the fourth memory unit;
wherein the processor determines the axis of the first probe (11) based on the data stored in the first memory unit, the second memory unit, and the third memory unit;
wherein the processor compares the coordinate information of the axis (L2) of the virtual puncture needle and the axis of the first probe (11), and sends a signal presenting a judgment of coincidence to the display when the processor finds that the axis of the first probe (11), and the axis (L2) of the virtual puncture needle coincide;
wherein the display emits green light when the display receives the signal presenting the judgment of coincidence from the processor;
wherein the planned path (L1) is determined by obtaining the position of a projection of the axis of the first probe (11) onto the plane containing the ultrasound image of the lesion through a planar matrix conversion;
wherein the ultrasound image of the lesion is fan-shaped, the virtual coordinate system takes the apex (C1) of the fan-shaped ultrasound image of the lesion as its origin, and the planar matrix conversion is performed according to a transformation formula I to obtain coordinate information of the projection of the axis of the first probe (11) onto the plane containing the ultrasound image of the lesion, the transformation formula I is given by:

$$(x',y',z',1) = T(x,y,z,1)^T,$$

wherein (x', y', z', 1) represents the coordinate information of a point on the axis of the first probe after the transformation, (x', y', z', 1)T represents the coordinate information of the point before the transformation, $$T = T_4 T_3 T_2 T_1,$$

$$T_4 = \begin{bmatrix} 1 & 0 & 0 & d_x \\ 0 & 1 & 0 & d_y \\ 0 & 0 & 1 & d_z \\ 0 & 0 & 0 & 1 \end{bmatrix},$$

$$\vec{d} = \left(-\overrightarrow{P_1 Q_1'} \cdot \vec{n_1}\right)\vec{n_1},$$

$$\vec{d} = (d_x, d_y, d_z),$$

$$Q_1' = T_3 T_2 T_1 Q_1,$$

-continued $$T_3 = \begin{bmatrix} 1 & 0 & 0 & q_x^1 \\ 0 & 1 & 0 & q_y^1 \\ 0 & 0 & 1 & q_z^1 \\ 0 & 0 & 0 & 1 \end{bmatrix},$$

$$T_2 = \begin{bmatrix} 1 & 0 & 0 & 0 \\ 0 & \cos\theta_x^1 & \sin\theta_x^1 & 0 \\ 0 & -\sin\theta_x^1 & \cos\theta_x^1 & 0 \\ 0 & 0 & 0 & 1 \end{bmatrix} \begin{bmatrix} \cos\theta_y^1 & 0 & \sin\theta_y^1 & 0 \\ 0 & 1 & 0 & 0 \\ -\sin\theta_y^1 & 0 & \cos\theta_y^1 & 0 \\ 0 & 0 & 0 & 1 \end{bmatrix} \begin{bmatrix} \cos\theta_y^2 & 0 & -\sin\theta_y^2 & 0 \\ 0 & 1 & 0 & 0 \\ \sin\theta_y^2 & 0 & \cos\theta_y^2 & 0 \\ 0 & 0 & 0 & 1 \end{bmatrix}$$

$$\begin{bmatrix} 1 & 0 & 0 & 0 \\ 0 & \cos\theta_x^2 & -\sin\theta_x^2 & 0 \\ 0 & \sin\theta_x^2 & \cos\theta_x^2 & 0 \\ 0 & 0 & 0 & 1 \end{bmatrix},$$

$$\cos\theta_x^2 = \frac{n_z^2}{\sqrt{(n_y^2)^2 + (n_z^2)^2}}, \sin\theta_x^2 = \frac{n_y^2}{\sqrt{(n_y^2)^2 + (n_z^2)^2}},$$

$$\cos\theta_y^2 = \frac{\sqrt{(n_y^2)^2 + (n_z^2)^2}}{\sqrt{(n_x^2)^2 + (n_y^2)^2 + (n_z^2)^2}}, \sin\theta_y^2 = \frac{n_x^2}{\sqrt{(n_x^2)^2 + (n_y^2)^2 + (n_z^2)^2}},$$

$$\cos\theta_x^1 = \frac{n_z^1}{\sqrt{(n_y^1)^2 + (n_z^1)^2}}, \sin\theta_x^1 = \frac{n_y^1}{\sqrt{(n_y^1)^2 + (n_z^1)^2}},$$

$$\cos\theta_y^1 = \frac{\sqrt{(n_y^1)^2 + (n_z^1)^2}}{\sqrt{(n_x^1)^2 + (n_y^1)^2 + (n_z^1)^2}}, \sin\theta_y^1 = \frac{n_x^1}{\sqrt{(n_x^1)^2 + (n_y^1)^2 + (n_z^1)^2}}.$$

$$\vec{n}_1 = (n_x^1, n_y^1, n_z^1), \vec{n}_2 = (n_x^2, n_y^2, n_z^2),$$

$$\vec{n}_1 = \frac{\overrightarrow{P_1P_2} \times \overrightarrow{P_1P_3}}{|\overrightarrow{P_1P_2}||\overrightarrow{P_1P_3}|}, \vec{n}_2 = \frac{\overrightarrow{Q_1Q_2} \times \overrightarrow{Q_1Q_3}}{|\overrightarrow{Q_1Q_2}||\overrightarrow{Q_1Q_3}|},$$

$$T_1 = \begin{bmatrix} 1 & 0 & 0 & -q_x^1 \\ 0 & 1 & 0 & -q_y^1 \\ 0 & 0 & 1 & -q_z^1 \\ 0 & 0 & 0 & 1 \end{bmatrix},$$

$P_1$, $P_2$, $P_3$ are three non-collinear sampling points on the plane $F_1$ containing the ultrasound image of the lesion, and $Q_1$, $Q_2$, $Q_3$ are three non-collinear points on the plane $F_2$ containing the axis of a virtual first probe, $P_1(p_x^1, p_y^1, p_z^1)$, $P_2(p_x^2, p_y^2, p_z^2)$, $P_3(p_x^3, p_y^3, p_z^3)$, $Q_1(q_x^1, q_y^1, q_z^1)$, $Q_2(q_x^2, q_y^2, q_z^2)$, $Q_3(q_x^3, q_y^3, q_z^3)$ are the coordinates of $P_1$, $P_2$, $P_3$, $Q_1$, $Q_2$, and $Q_3$, the virtual first probe is at least partially determined by the first positioning devices (4) on the first probe (11), $\vec{n}_1$ is a unit normal vector of the plane $F_1$ containing the ultrasound image of the lesion, and $\vec{n}_2$ is a unit normal vector of the plane $F_2$, dx represents a component of the vector $-\overrightarrow{P_1Q_1}$ in the equation $\vec{d} = (-\overrightarrow{P_1Q_1} \cdot \vec{n}_1)\vec{n}_1$ in an x-direction, dv represents a component of the vector $-\overrightarrow{P_1Q_1}$ in a v-direction, dz represents a component of the vector $-\overrightarrow{P_1Q_1}$ in a z-direction.

2. The puncture needle positioning system according to claim 1, wherein the first probe (11) is provided with three of the plurality of first positioning devices (4), the three of the the plurality of first positioning devices (4) and the axis of the first probe are in the same plane, two of the three of the plurality of first positioning devices (4) are located on a cross section of the first probe (11), the cross section is perpendicular to the axis of the first probe (11), and the three of the plurality of first positioning devices (4) constitute the vertices of a right triangle.

3. The puncture needle positioning system according to claim 1, wherein two of the plurality of second positioning devices (5) are arranged on the puncture needle, and the second positioning devices (5) are arranged on an axis of the puncture needle.

4. The puncture needle positioning system according to claim 1, wherein both the first positioning devices (4) and the second positioning devices (5) are selected from sensors.

5. The puncture needle positioning system according to claim 1, wherein the ultrasound unit (1) also includes a second probe (12) for monitoring the puncture process.

6. The puncture needle positioning system according to claim 1, wherein according to the coordinate information of the second positioning devices (5) in the virtual coordinate system,
the planar matrix conversion is performed by the processor to obtain transformed coordinate information of the axis (L2) of the virtual puncture needle, the axis (L2) of the virtual puncture needle is obtained by projecting the axis of the puncture needle onto the plane containing the ultrasound image of the lesion,
the planar matrix conversion is performed by the processor to obtain transformed coordinate information of the apex (C2) of the virtual puncture needle, the apex (C2) of the virtual puncture needle is obtained by projecting the apex of the puncture needle onto the plane containing the ultrasound image of the lesion,
the axis and apex of the virtual puncture needle are then displayed in the virtual coordinate system according to their transformed coordinate information.

7. The puncture needle positioning system according to claim 1, wherein in the virtual coordinate system, the apex (C2) of the virtual puncture needle is compared with the apex (C1) of the ultrasound image of the lesion to see if they coincide, and the direction of the axis (L2) of the virtual puncture needle is compared with the direction of the planned path (L1) to see if they coincide,
wherein when the apex (C2) of the virtual puncture needle and the apex (C1) of the ultrasonic image coincide, and the direction of the axis (L2) of the virtual puncture needle and the the direction of the planned path (L1) coincide, the judgment of coincidence is returned.

8. The puncture needle positioning system according to claim 2, wherein the first probe (11) is provided with a probe clamp (6) that matches the first probe (11), the probe clamp (6) is provided with three first insertion holes for installing the first positioning devices (4), and the positions of the three of the plurality of first insertion holes match the three first positioning devices (4).

9. The puncture needle positioning system according to claim 3, wherein the puncture needle is provided with a puncture needle clamp (7) matched with the puncture needle, and the puncture needle clamp (7) is provided with two second insertion holes for installing the second positioning devices (5), and the positions of the two second insertion holes relative to each other match the positions of the two of the plurality of second positioning devices (5) relative to each other.

* * * * *